(12) United States Patent
Kazerooni et al.

(10) Patent No.: US 10,682,249 B2
(45) Date of Patent: Jun. 16, 2020

(54) CONTROLLABLE PASSIVE ARTIFICIAL KNEE

(71) Applicant: THE REGENTS OF THE UNIVERSITY OF CALIFORNIA, Oakland, CA (US)

(72) Inventors: Homayoon Kazerooni, Berkeley, CA (US); Wayne Tung, Berkeley, CA (US); Don Jin Hyun, Cambridge, MA (US); Stephen McKinley, Berkeley, CA (US); Yoon Jung Jeong, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/641,039

(22) Filed: Mar. 6, 2015

(65) Prior Publication Data
US 2015/0173929 A1 Jun. 25, 2015

Related U.S. Application Data

(63) Continuation of application No. PCT/US2013/046478, filed on Jun. 19, 2013.
(Continued)

(51) Int. Cl.
*A61F 5/01* (2006.01)
*A61H 1/02* (2006.01)
(Continued)

(52) U.S. Cl.
CPC .......... *A61F 5/0123* (2013.01); *A61F 5/0125* (2013.01); *A61H 1/00* (2013.01);
(Continued)

(58) Field of Classification Search
CPC ........ A61F 5/01; A61F 5/0102; A61F 5/0123; A61F 5/0125; A61F 2005/0155;
(Continued)

(56) References Cited

U.S. PATENT DOCUMENTS 5,476,441 A * 12/1995 Durfee et al. .................. 602/23
6,635,024 B2 10/2003 Hatton et al.
(Continued)

FOREIGN PATENT DOCUMENTS

CN 101677866 A 3/2017
CN 2921182 5/2018
(Continued)

OTHER PUBLICATIONS

International Search Report, dated Sep. 30, 2013, International Search Authority, United States Patent & Trademark Office U.S.A.
(Continued)

*Primary Examiner* — Keri J Nelson
*Assistant Examiner* — Michelle J Lee
(74) *Attorney, Agent, or Firm* — Kwan & Olynick LLP

(57) ABSTRACT

An exoskeleton (100) adapted to be coupled to a lower extremity of a person includes a thigh link (102), a shank link (104) and a knee joint (106) allowing flexion and extension between the thigh and shank links (102, 104). A torque generator (156) connected to the knee joint (106) includes a wrap spring (110) having a first end (112) coupled to the thigh link (102), and a second end (118) coupled to an electric actuator (116) capable of selectively positioning the second end (118) of the wrap spring (110). A controller (120) causes the electric actuator (116) to position the wrap spring (110) to provide a selective torque between the thigh and shank links (102, 104) based on a signal (212, 214, 216) produced by a sensor (164, 166, 168).

28 Claims, 28 Drawing Sheets

Related U.S. Application Data

(60) Provisional application No. 61/697,948, filed on Sep. 7, 2012.

(51) Int. Cl.
    *A61H 3/00*     (2006.01)
    *B25J 9/00*     (2006.01)
    *A61H 1/00*     (2006.01)

(52) U.S. Cl.
    CPC ............ *A61H 1/001* (2013.01); *A61H 1/0244* (2013.01); *A61H 3/00* (2013.01); *B25J 9/0006* (2013.01); *A61F 2005/0158* (2013.01); *A61H 2201/0165* (2013.01); *A61H 2201/1215* (2013.01); *A61H 2201/163* (2013.01); *A61H 2201/165* (2013.01); *A61H 2201/1642* (2013.01); *A61H 2201/5007* (2013.01); *A61H 2201/5069* (2013.01)

(58) Field of Classification Search
    CPC ...... A61F 2005/0158; A61F 2005/0169; A61F 2005/0132–0179; A61F 2/60–646; A61F 2/68; A61F 2002/648; A61F 2002/6845; A61F 2002/6854; A61F 2002/701; A61F 2002/704; A61H 1/00; A61H 1/001; A61H 1/0214; A61H 1/0237; A61H 1/0244; A61H 1/0255; A61H 1/0262; A61H 3/00; B25J 9/0006
    See application file for complete search history.

(56) References Cited

U.S. PATENT DOCUMENTS

| | | | |
|---|---|---|---|
| 7,153,242 B2 | 12/2006 | Goffer | |
| 7,628,766 B1 | 12/2009 | Kazerooni | |
| 7,883,546 B2 | 2/2011 | Kazerooni et al. | |
| 8,057,410 B2* | 11/2011 | Angold et al. | 601/5 |
| 8,070,700 B2 | 12/2011 | Kazerooni et al. | |
| 8,231,688 B2 | 7/2012 | Fairbanks et al. | |
| 2002/0169402 A1 | 11/2002 | Hatton et al. | |
| 2003/0062241 A1* | 4/2003 | Irby | A61F 5/0125 192/81 C |
| 2003/0153854 A1* | 8/2003 | Nijenbanning et al. | 602/16 |
| 2004/0267379 A1 | 12/2004 | Pasolini | |
| 2005/0251079 A1 | 11/2005 | Carvey et al. | |
| 2008/0039756 A1 | 2/2008 | Thorsteinsson et al. | |
| 2008/0200856 A1* | 8/2008 | Cadichon | 602/32 |
| 2009/0292369 A1* | 11/2009 | Kazerooni et al. | 623/27 |
| 2010/0023133 A1 | 1/2010 | Fairbanks et al. | |
| 2010/0094185 A1 | 4/2010 | Amundson et al. | |
| 2010/0113980 A1 | 5/2010 | Herr et al. | |
| 2010/0121232 A1* | 5/2010 | Sankai | A61H 3/008 601/23 |
| 2010/0125229 A1 | 5/2010 | Rudolph | |
| 2010/0204627 A1* | 8/2010 | Kazerooni et al. | 602/16 |
| 2011/0009787 A1 | 1/2011 | Pallari et al. | |
| 2011/0105966 A1 | 5/2011 | Kazerooni et al. | |
| 2011/0266323 A1 | 11/2011 | Kazerooni et al. | |
| 2012/0101415 A1 | 4/2012 | Goffer et al. | |
| 2012/0172770 A1 | 7/2012 | Almesfer et al. | |
| 2012/0215323 A1* | 8/2012 | Seyr | A61F 2/64 623/24 |

FOREIGN PATENT DOCUMENTS

| | | |
|---|---|---|
| CN | 104822346 B | 5/2018 |
| CN | 108742967 A | 11/2018 |
| EP | 2189136 A1 | 5/2010 |
| JP | 2009066395 A | 4/2009 |
| JP | 6535283 | 6/2019 |
| WO | 9409727 A2 | 5/1994 |
| WO | 0143669 A1 | 6/2001 |
| WO | 2011026086 A1 | 3/2011 |

OTHER PUBLICATIONS

Extended European Search Report dated Aug. 3, 3015 in a corresponding application No. EP13835254.
"European Application Serial No. 13835254.7, Office Action dated Aug. 10, 2016", 5 pgs.
"Chinese Application Serial No. 2013800583371, Notice of Allowance dated Feb. 2, 2018", 3 pgs.
"Chinese Application Serial No. 2013800583371, Office Action dated May 24, 2017", 22 pgs.
"European Application Serial No. 18164129.1, Search Report dated Jun. 27, 2018", 7 pgs.
"Japanese Application Serial No. 2015-531067, Office Action dated May 15, 2018", 11 pgs.
"Japanese Application Serial No. 2015-531067, Office Action dated Jun. 6, 2017", 6 pgs.
"Japanese Application Serial No. 2015-531067, Notice of Allowance dated May 14, 2019", 11 pgs.

* cited by examiner

CONTROLLABLE PASSIVE ARTIFICIAL KNEE

TECHNICAL FIELD

The present invention pertains to the art of artificial lower limb prosthetics and orthotic systems: more particularly, to an exoskeleton knee that can be used for a variety of orthotic applications.

BACKGROUND ART

A traditional knee-ankle-foot orthosis (KAFO) is used to increase the patient stability during the weight-bearing phase of walking. A traditional KAFO locks the knee in full extension, which provides stability. This locked posture results in patients' ability to ambulate with gait deviations that can lead to overuse injuries. A stance control orthosis (SCO) allows the knee to flex during the swing phase of the gait cycle and prevents knee flexion for stability during the stance phase. By allowing the knee to bend during the swing phase, SCOs allow a more natural gait, which may reduce secondary complications from gait compensations and allow the patient to walk with less effort. There are several stance control orthoses (prior art).

Fillauer developed a gravity-actuated knee joint locking system for its Swing Phase Lock (SPL) orthosis (U.S. Patent20030153854). A Swing Phase Lock uses a simple internal pendulum mechanism mounted on the thigh link (the member that moves in unison with the user's thigh). As the thigh link moves, the pendulum swinging motion locks and unlocks the shank link (the member that moves in unison with the user's shank) relative to the thigh link. This allows for locking and unlocking of the knee joint for appropriate phases of a walking cycle.

Free Walk orthosis (marketed by Ottobock) and UTX orthosis (marketed by Becker) work based on the principle. The dorsiflexion of the foot at the end of the stance pulls on controllable cable connected to a locking mechanism at the knee joint. This pulling action disengages the locking mechanism for swing. The locking mechanism is spring loaded and locks the knee when the knee is fully extended.

Sensor Walk (manufactured by Ottobock) uses a wrap spring at the knee joint for locking and unlocking the knee. This orthosis includes two sets of sensors—one at the knee to measure the knee angle and another at the footplate to measure force between the foot and the floor; a wrap spring clutch replacing the lateral knee joint to provide braking capability to support the anatomic knee joint; a microprocessor-controlled release for the brake; electronic circuitry; and a battery pack carried in a waist pack. Sensors in the footplate disengage the wrap spring clutch and allow the knee to bend in the late stance phase, when weight has been transferred to the contralateral side and is ready for single-limb support. A knee sensor senses extension of the knee after toe off and sends a signal to the microprocessor putting the wrap spring clutch in its locked position.

Horton Stance Control Orthosis (U.S. Pat. No. 6,635,024 and U.S. 200220169402) includes a locking mechanism that locks and unlocks the knee with the help of a push rod. The push rod is placed between the heel and the knee. The push rod locks the knee at heel strike and unlocks the knee right at the end of stance phase. The device locks knee at any angle.

DISCLOSURE OF INVENTION

The present invention is directed to exoskeleton systems which include at least an exoskeleton knee with controllable resisting torque. In particular, the invention here describes an exoskeleton knee and its applications in a variety of exoskeleton systems where friction forces between two surfaces are used to impede the knee flexion and extension motion in various phases of a walking cycle. By controlling the friction forces between two surfaces, arbitrary resistive torques for the exoskeleton knee during some portions of the locomotion cycles can be provided. Creating an impeding torque at the exoskeleton knee will decrease the torque that needs to be provided by the wearer at his/her knee. Additionally, the exoskeleton knee will unload the wearer's knee during most portions of stance phase. The exoskeleton knee described here can be worn not only independently on the wearer's knee but also in conjunction with hip, ankle or foot exoskeletons. This gives a great deal of flexibility for use of exoskeleton knees in variety of medical, civilian and military applications.

MODES FOR CARRYING OUT THE INVENTION

Figure 1:
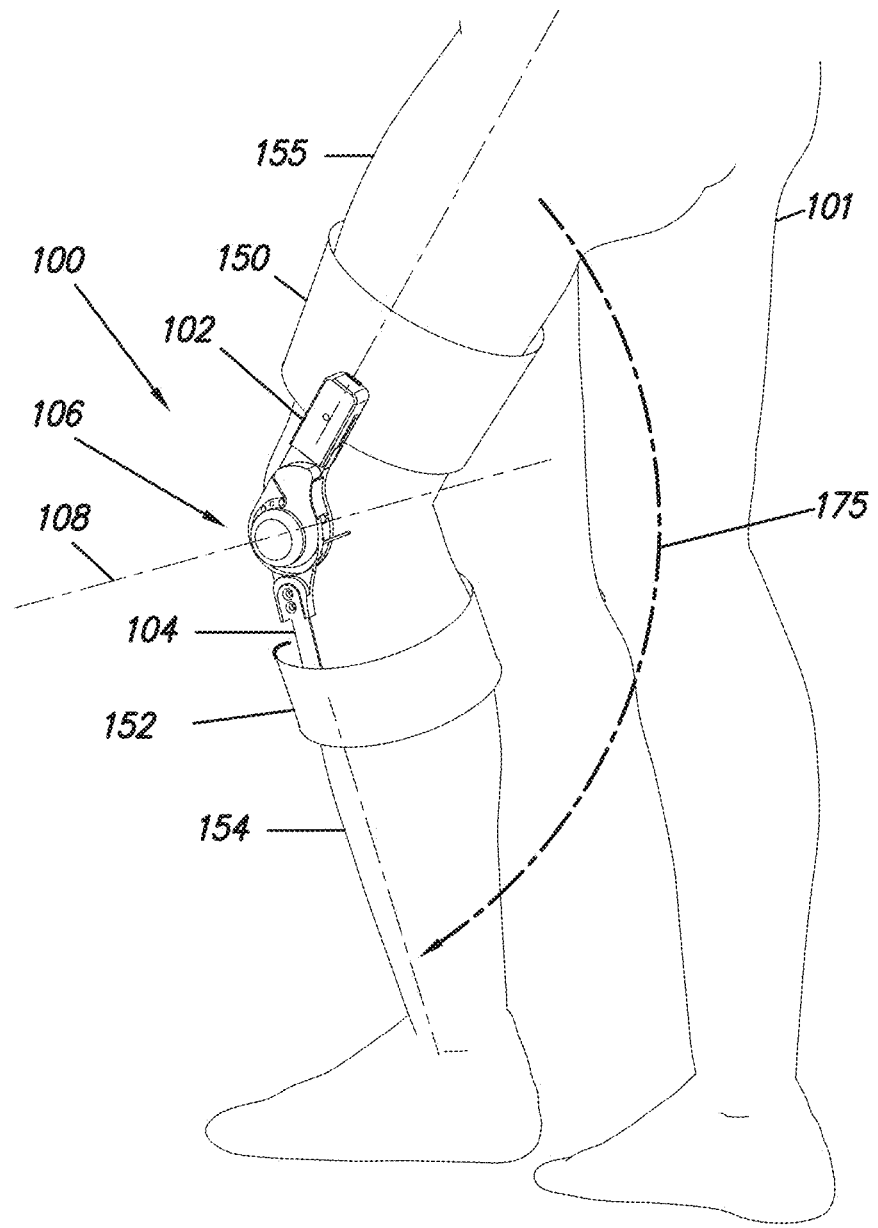
FIG. 1 depicts an embodiment of the exoskeleton of the present invention.

FIG. 1 shows an embodiment of an exoskeleton 100 which is coupled to a user 101. Exoskeleton 100 comprises a first link or thigh link 102, a second link or shank link 104 and a knee joint 106 configured to allow flexion and extension rotations between thigh link 102 and shank link 104 along a knee axis 108. It should be understood that the first link is configurable to move in unison with a user's thigh and the second link is configurable to move in unison with the user's shank. Extension rotation indicates the motion of shank link 104 and thigh link 102 when shank link 104 and thigh link 102 move away from each other. Arrow 175 shows the direction of the extension movement of shank link 104 relative to thigh link 102. Flexion rotation indicates the motion of shank link 104 and thigh link 102 when shank link 104 and thigh link 102 move close to each other. In some embodiments of the invention, exoskeleton 100 further comprises a thigh connector 150 that allows coupling to a user's thigh 155. In some embodiments of the invention, exoskeleton 100 further comprises a shank connector 152 that allows coupling to a user's shank 154. In some embodiments of the inventions thigh connector, 150 and shank connector 152 comprise braces. Although braces have been used to demonstrate the coupling of shank link 104 and thigh link 102 to the user's thigh 155 and shank 154 in FIG. 1, an ordinary person skilled in the art would understand that many methods and devices can be employed that would cause shank link 104 and thigh link 102 to move in unison with user's shank 154 and user's thigh 155; coupling through shank and thigh braces is only one method of causing the unison movement.

Figure 2:
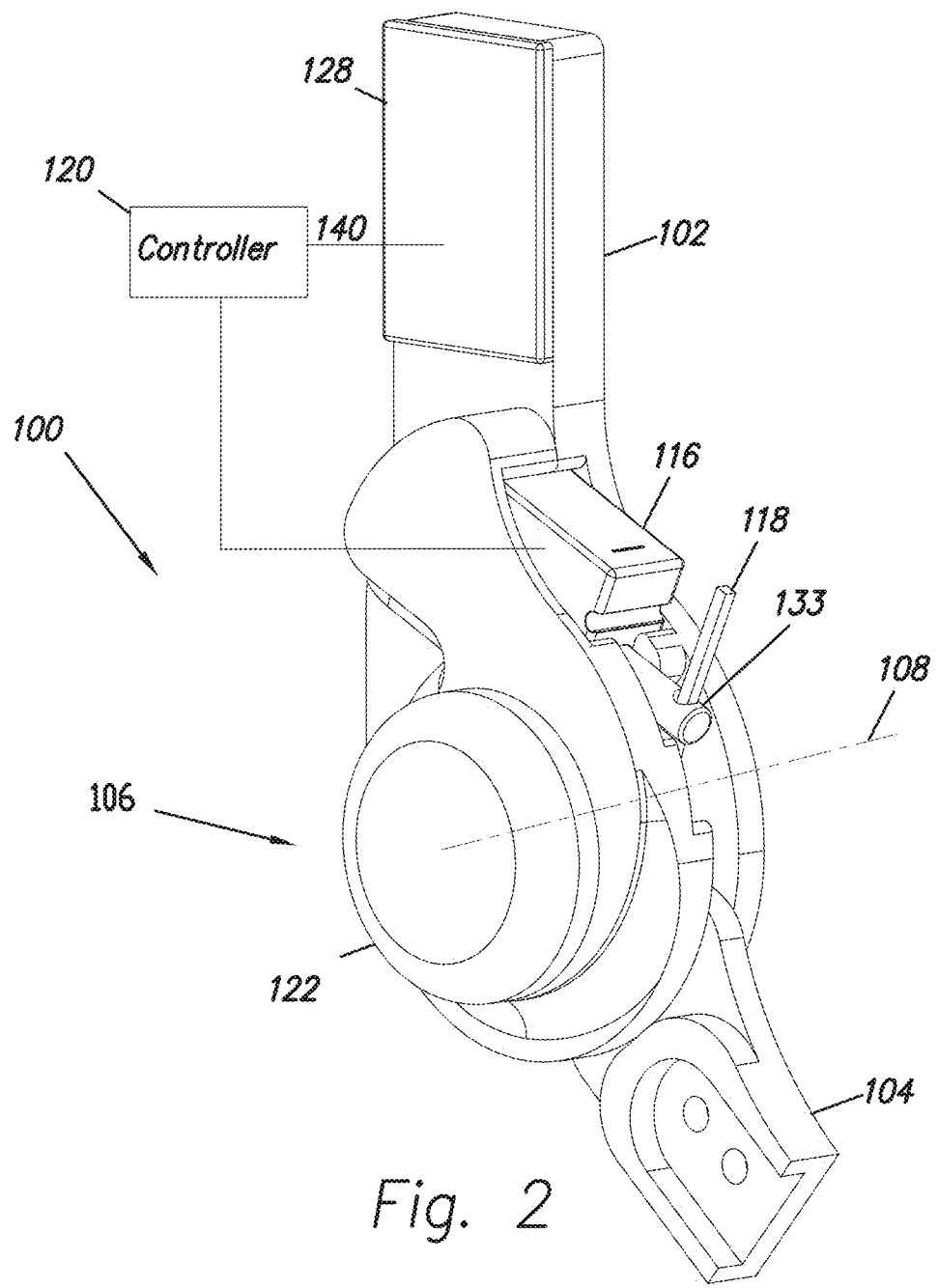
FIG. 2 depicts an embodiment of the exoskeleton where braces have been removed for clarity.
Figure 3:
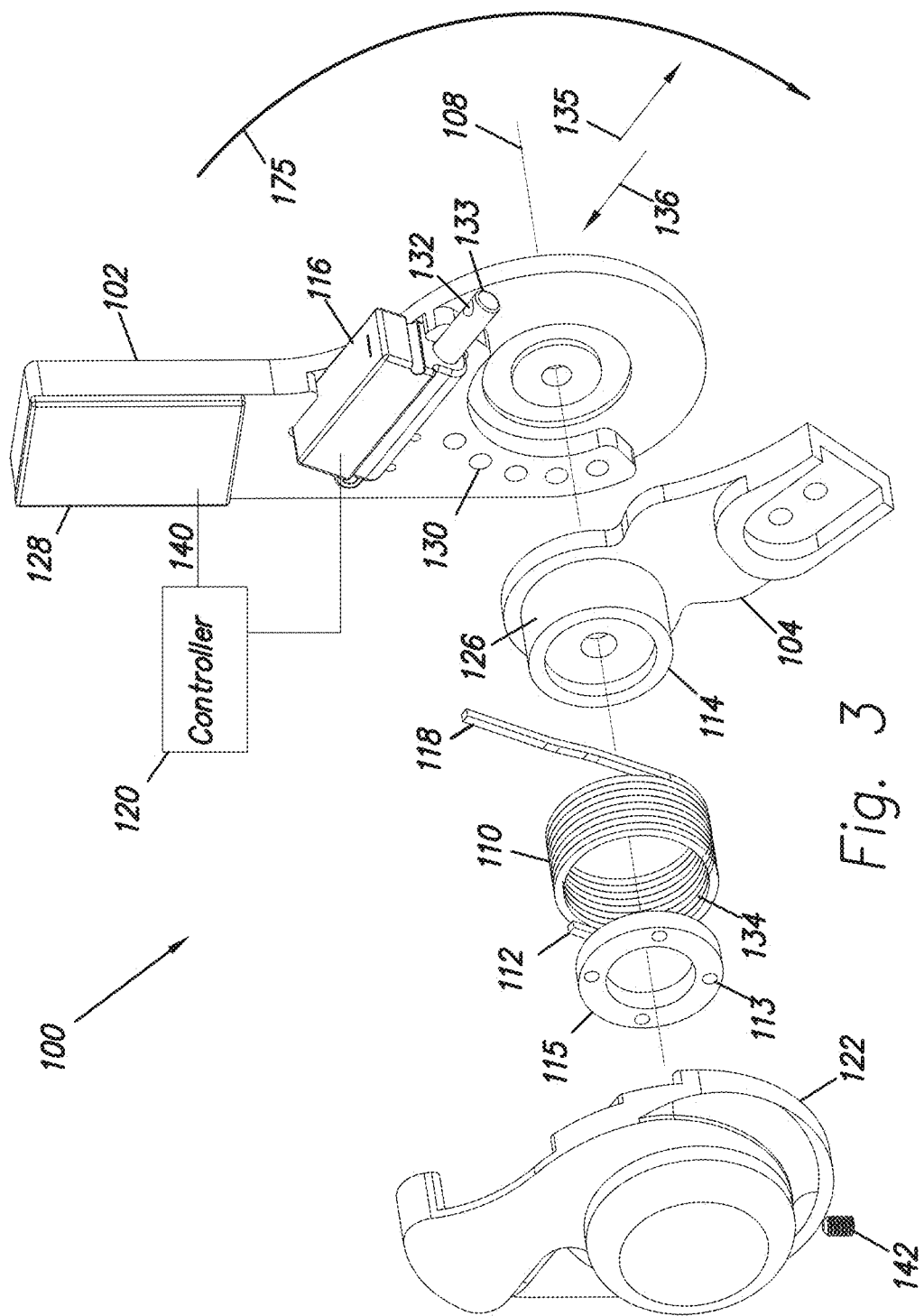
FIG. 3 is an exploded view of the exoskeleton of FIG. 2.
Figure 4:
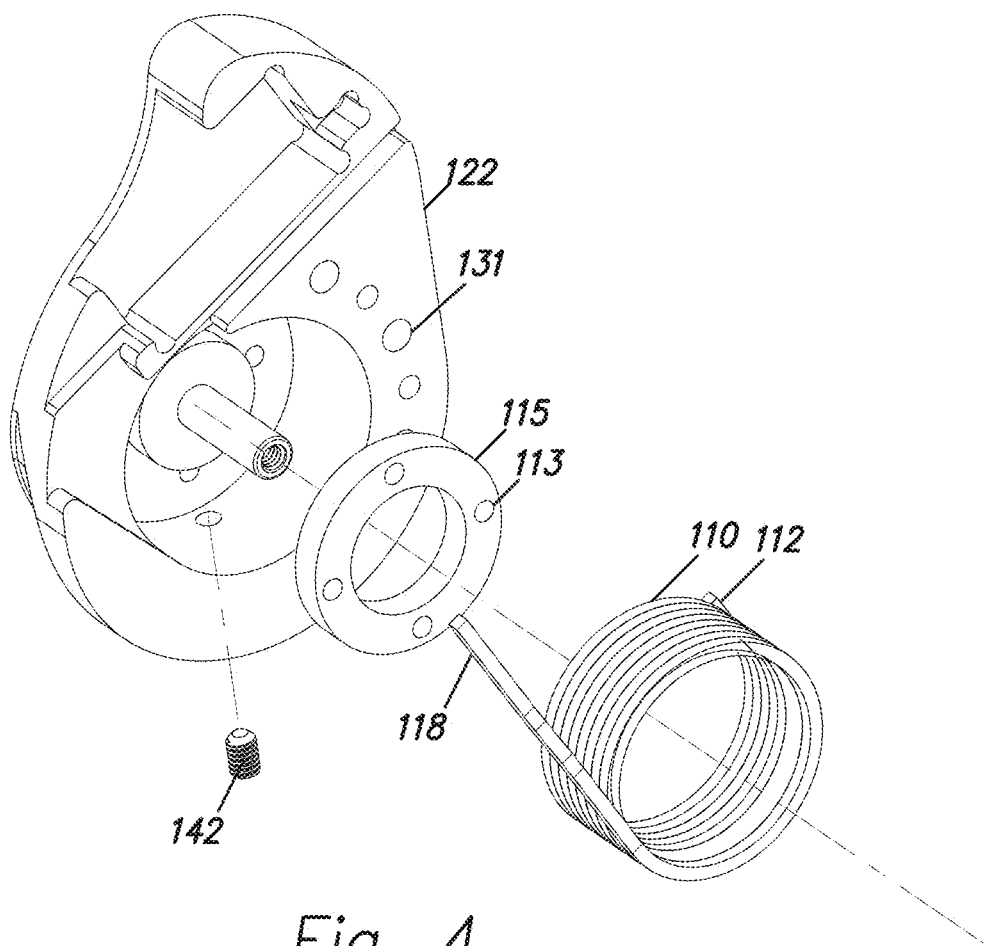
FIG. 4 is an exploded view that depicts a coupling of a wrap spring to a thigh link.
Figure 5:
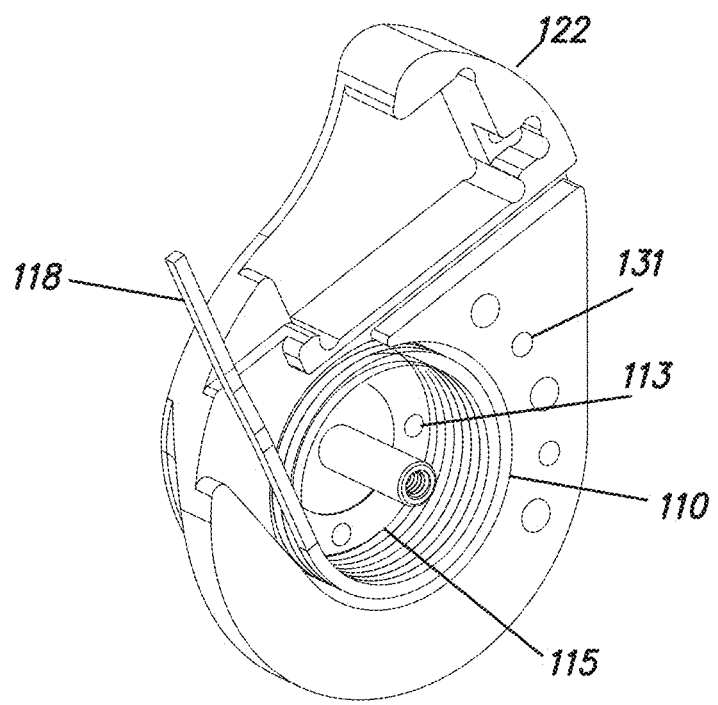
FIG. 5 depicts the assembled coupling of FIG. 4.

FIG. 2 shows an embodiment of exoskeleton 100 where braces 150 and 152 have been removed for clarity. FIG. 3 is an exploded view of the exoskeleton 100 of FIG. 2, where braces are removed for clarity. Exoskeleton 100 further comprises a wrap spring 110 where a first end 112 of wrap spring 110 is coupled to thigh link 102. This coupling can be accomplished by a variety of mechanical methods; however, an embodiment of this coupling is described below with the help of FIG. 4 and FIG. 5. The coupling of wrap spring 110 to thigh link 102 has been facilitated through a disk 115 and a cap 122. FIG. 4 shows another view of cap 122, disk 115 and wrap spring 110. The first end 112 of wrap spring 110 is connected to cap 122. The wrap spring 110 is wrapped around disk 115. Disk 115 is then secured to cap 122 by four fasteners (not shown) passing through holes 113. A set screw 142 is then used to ensure wrap spring 110 does not rotate relative to disk 115. Cap 122 is coupled to thigh link 102 through fasteners (not shown) passing through a set of holes 130 and 131 (shown in FIGS. 3 and 4, respectively). This method secures first end 112 of wrap spring 110 to thigh link 102. Exoskeleton 100 additionally comprises a cylinder 114 coupled to shank link 104. Cylinder 114 is located substantially inside wrap spring 110 with its major axis substantially parallel to the major axis of wrap spring 110. Exoskeleton 100 further comprises at least one electric actuator 116 capable of positioning the second end 118 of wrap spring 110. When assembled, second end 118 extends through, and is retained within, a hole 132 in a bar 133 of actuator 116. Although actuator 116, in this embodiment, allows for linear motion of bar 133 along arrow 135 and 136, it should be appreciated that one can use a variety of actuators to control the position of second end 118 of wrap spring 110. Exoskeleton 100 further comprises a controller 120 capable of controlling electric actuator 116. In operation, controller 120 causes electric actuator 116 to position second end 118 of wrap spring 110 to provide arbitrary pressure between a cylindrical surface 126 of cylinder 114 and an inner surface 134 of wrap spring 110. This pressure causes a resistive torque between cylinder 114 and wrap spring 110. Consequently, the resistive torque between thigh link 102 and shank link 104 can be controlled by controlling second end 118 of wrap spring 110. As second end 118 moves with the help of actuator 116 along arrow 136, the resistive torque between thigh link 102 and shank link 104 increases. As second end 118 moves with the help of actuator 116 along arrow 135, the resistive torque between thigh link 102 and shank link 104 decreases.

FIG. 1 through FIG. 5 show an embodiment of the exoskeleton 100 where controllable resistive torque is generated by use of friction forces between two friction surfaces. As best shown in FIG. 3, the first friction surface is the outer surface 126 of a cylinder 114 coupled to shank link 104, and the second friction surface is the inner surface 134 of wrap spring 110 coupled to thigh link 102 through disk 115 and cap 122. Electric actuator 116, preferably coupled to thigh link 102, positions the second end 118 of wrap spring 110 and controls the pressure between outer surface 126 of cylinder 114 and inner surface 134 of wrap spring 110. Consequently, the resistive torque between thigh link 102 and shank link 104 can be controlled. An ordinary person skilled in the art can use the above approach with the reverse connection (not shown). This means, in this reverse case, first end 112 of the spring 110 is coupled to shank link 104 and cylinder 114 is coupled to thigh link 102. Further, in this reverse case, electric actuator 116 is preferably coupled to shank link 104.

Figure 26:
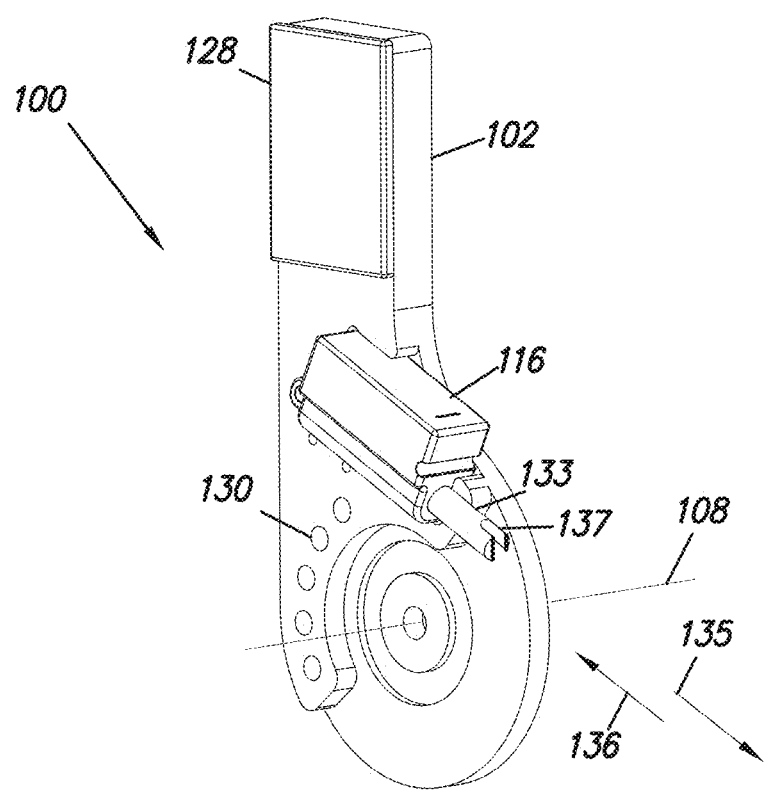
FIG. 26 shows an embodiment of the invention where the wrap spring is unconstrained by the actuator and is free to move along direction 135.
Figure 27:
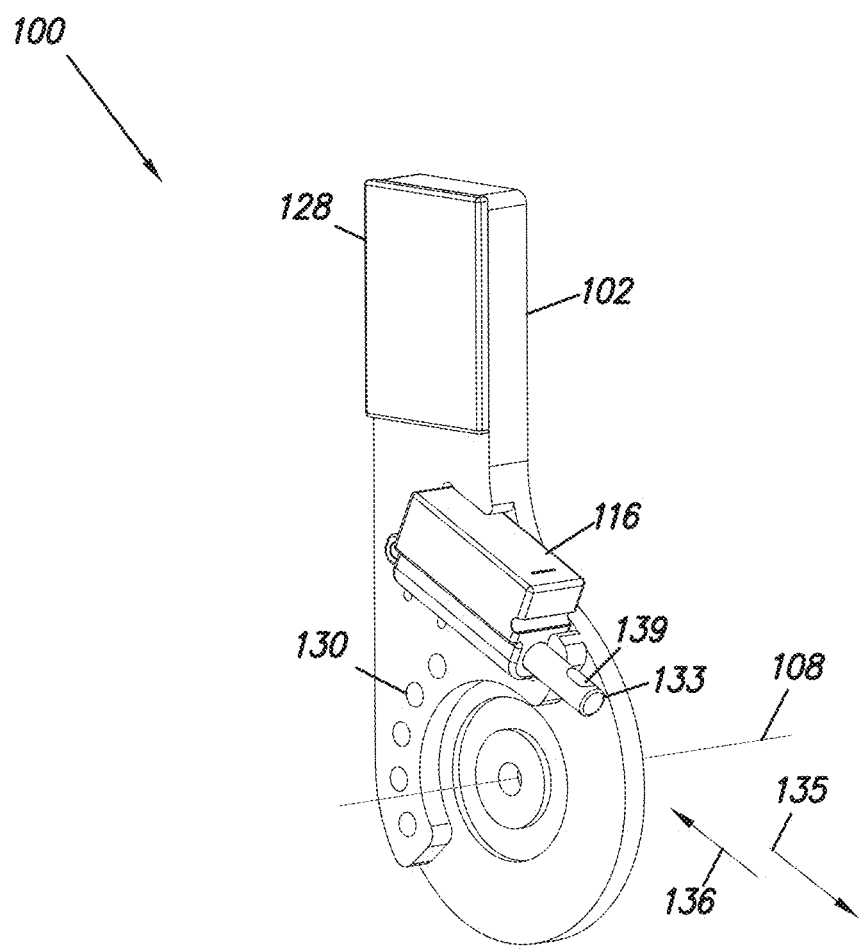
FIG. 27 shows an embodiment of the invention where the wrap spring is unconstrained by the actuator and is free to move along direction 135.
Figure 28:
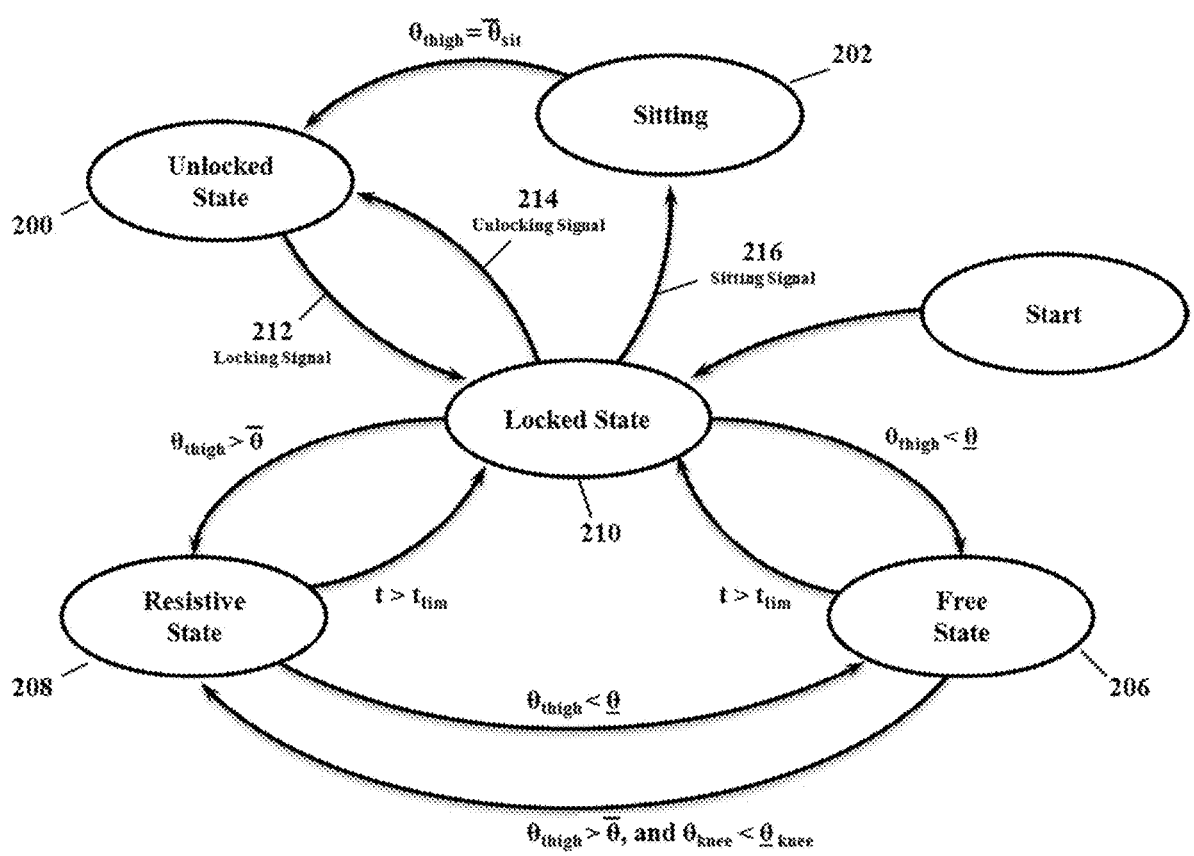
FIG. 28 shows another embodiment of the finite state machine associated with the exoskeleton control.

In one embodiment of the invention, the outer diameter of cylinder 114 is slightly larger than the inner diameter of wrap spring 110. In this embodiment, inner surface 134 of wrap spring 110, in its free configuration (i.e. when second end 118 of warp spring 110 is unconstrained by actuator 116), is in contact with the outer surface of cylinder 114. This allows for a snug fit between wrap spring 110 and cylinder 114 when second end 118 of wrap spring 110 is not constrained by actuator 116 and is free to move. In this embodiment, as shown in FIG. 26, one has an option of coupling actuator 116 to second end 118 of wrap spring 110, such that second end 118 of wrap spring 110 is unconstrained by actuator 116 and is free to move along arrow 135. This allows for free motion of second end 118 of wrap spring 110 to unwind wrap spring 110, since second end of warp spring can freely move in slot 137 provided in bar 133. The special property of this embodiment is that it allows for free knee extension (or with a very little resistance during knee extension) of thigh link 102 and shank link 104 relative to each other at all times. Since wrap spring 110 and cylinder 114 are in contact with each other when second end 118 of wrap spring 110 is unconstrained, then to provide selective resistive torque, it is necessary to use actuator 116 to move second end 118 of the warp spring 110 along direction 135 to unravel wrap spring 110. The more actuator 116 moves second end 118 of wrap spring 110 along direction 135, the more wrap spring 110 will unravel and less resistive torque will be produced. If second end 118 of wrap spring 110 is moved along direction 135 to a point that there is very minimal contact (or no contact) between wrap spring 110 and cylinder 114, then no resistive torque is created between the inner surface of wrap spring 110 and cylinder 114. In this embodiment, regardless of position of second end 118 of wrap spring 110 (i.e. regardless of how much resistive torque is produced in response to flexion between thigh link 102 and shank link 104), cylinder 114 (and consequently shank link 104) can turn freely along arrow 175 with respect to thigh link 102. In this embodiment, thigh link 102 and shank link 104 can extend relative to each other freely (or with a very little resistance) at all times even when resistive torque is produced in response to flexion between thigh link 102 and shank link 104. This property is important because it allows the knee joint to extend freely or with little resistance at all times without requiring any command to actuator 116. In this embodiment, actuator 116 is responsible only for producing selective resistive torque during flexion between shank link 104 and thigh link 102. The mechanical nature of this embodiment allows for free extension of shank link 104 and thigh link 102 relative to each other at all times. It can be understood that instead of creating slot 137 in bar 133, one can make an elongated hole (now 139) as shown in FIG. 27.

Figure 6:
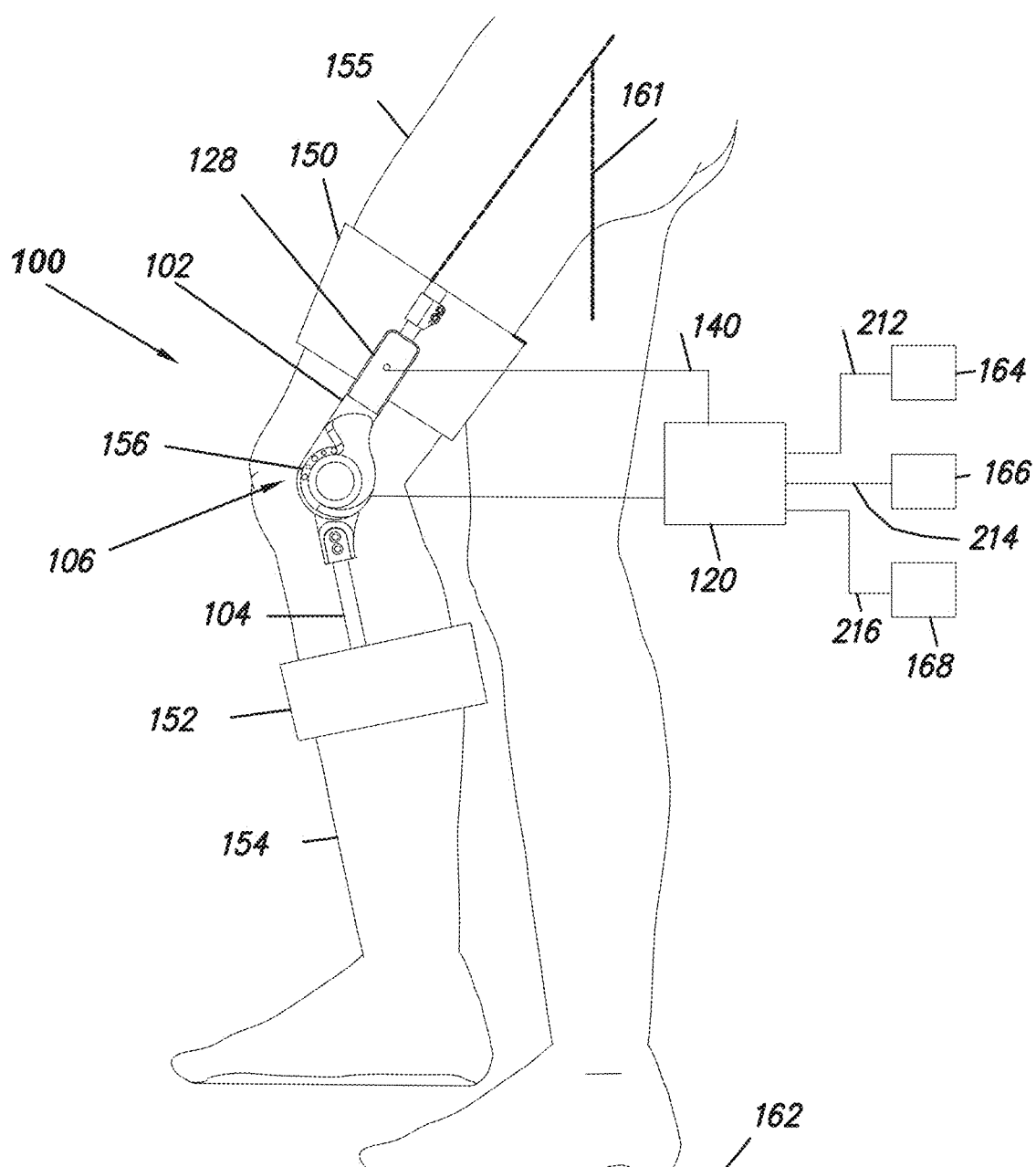
FIG. 6 shows an embodiment of the invention and its controller.

FIG. 6 shows an embodiment of the invention and its controller 120 regardless of how the controllable resistive torque is generated. Exoskeleton 100 is configurable to be coupled to a lower extremity of a person as shown in FIG. 6. Exoskeleton 100 comprises of thigh link 102, which is configurable to move in unison with user's thigh 155, shank link 104, which is configurable to move in unison with the user's shank 154, knee joint 106, which is configured to allow flexion and extension between shank link 104 and thigh link 102, a torque generator 156 configured to create a controllable resistive torque between shank link 104 and thigh link 102, at least one leg sensor 128 creating a leg signal 140 representing the angle of thigh link 102, and a controller 120 capable of controlling torque generator 156.

Torque generator 156 represents the general mechanism that generates resistive torques including other methods separate from friction forces. In particular, torque generator 156 can be configured to create a controllable resistive torque between thigh link 102 and shank link 104 by use of the friction force between two friction surfaces as depicted in FIG. 1 through FIG. 5. In some embodiments of the invention, hydraulic systems (not shown) may be used to provide controllable resistive torques (similar to hydraulic prosthetic knees) between thigh link 102 and shank link 104. In some other embodiments of the invention, electric motors and actuators (not shown) may be used to provide controllable resistive torques.

In some embodiments of the invention, leg sensor 128 comprises a sensor or a combination of sensors that can yield, with the help of a computer or an electric circuitry or both, the absolute angle of the thigh link 102. In some embodiments of the invention one can use an electronic printed circuit board (PCB) that includes a gyroscope, an accelerometer and a magnetometer. In some embodiments of the invention, the PCB sensor is mounted on the thigh link 102 for measuring the thigh link absolute angle. The PCB sensor may further include a microcomputer for filtering and computation. The gyroscope on the PCB outputs signals that represent the angular velocities of the PCB or any member that they PCB is connected to. In some embodiments of the invention, the gyroscope outputs signals that represent the angular velocities of the thigh link 102. The gyroscope outputs are then integrated to compute and generate the absolute angle of the PCB sensor or thigh link 102. The accelerometer and magnetometer on the PCB board are used to reduce the error in computation of the absolute angles from angular velocities. In some embodiments of the invention, leg sensor 128 includes its own computing capability and electronic circuitry for computation of the thigh link 102. In some embodiments of the invention, exoskeleton controller 120 is used to derive the absolute angle of the thigh link 102. The leg signal 140 indicates a signal, a combination of signals or at least a variable in the controller representing the absolute angle of thigh link 102 relative to a vertical gravitational line 161 (FIG. 7) or ground 162 (FIG. 6). In some embodiments, one can use the sensor on-board computer to generate leg signal 140. In some embodiments, one can use exoskeleton controller 120 or another computer or circuitry to generate leg signal 140.

Figure 20:
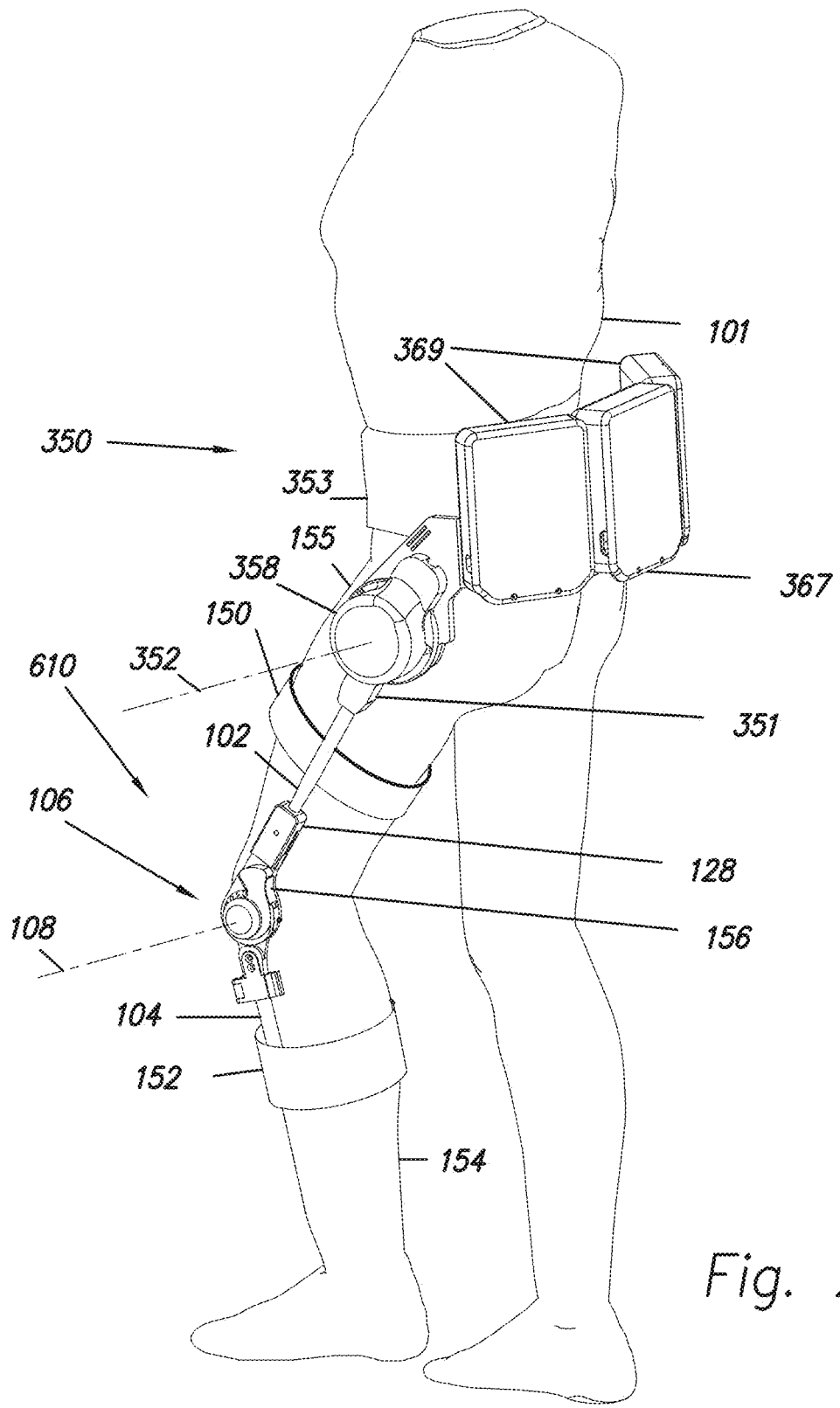
FIG. 20 shows an embodiment of the invention further comprising an exoskeleton trunk.

Since the person's torso (upper body) orientation is rather vertical during walking, then one can use a signal representing the angle between the user's torso and thigh link 102 as leg signal 140. This can be accomplished by installing sensors on the hip joint to measure the flexion and extension between thigh link 102 and torso link 353 along flexion extension axis 352 as shown in FIG. 20. Examples of leg sensor 128 include, without limitation, rotary potentiometers, linear potentiometers, magnetic encoders, optical encoders, linear variable differential transformers, capacitive displacement sensors, eddy current proximity sensors, variable-inductance proximity sensors, rocker switches, slide switches, accelerometer, inertial measurement units, gyroscopes, magnetometer and combinations thereof. In some embodiments of the invention, controller 120 is coupled to thigh link 102. In some embodiments of invention, controller 120 is coupled to shank link 104.

Figure 7:
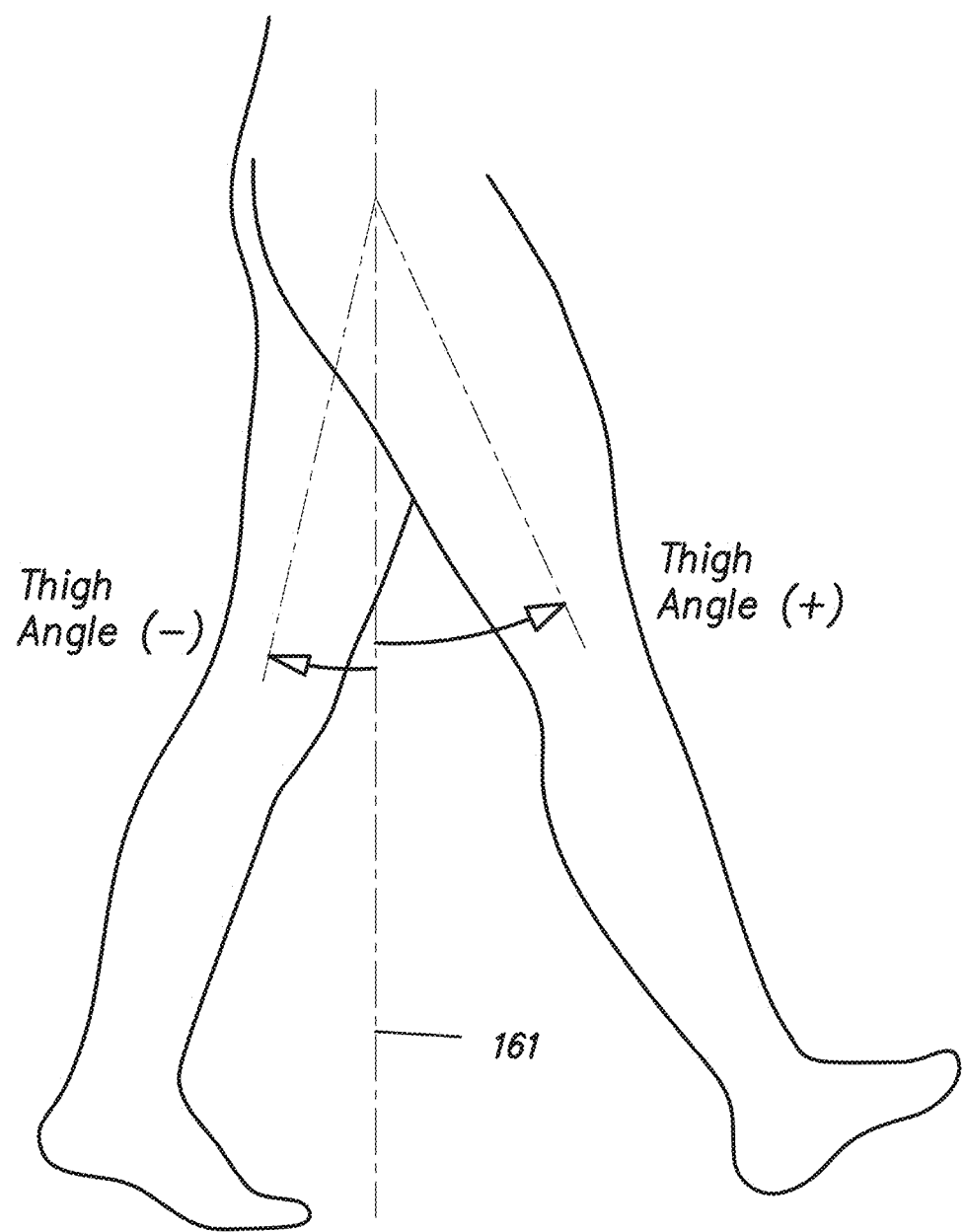
FIG. 7 depicts an absolute angle of a thigh link or a user's thigh relative to a vertical gravitational line.

In one embodiment of exoskeleton 100, leg signal 140 is a signal that represents the absolute angle of thigh link 102 relative to vertical gravitational line 161 as shown in FIG. 7. Vertical gravitational line 161 is parallel to gravitational force. A leg sensor 128 in the form of an inertial measurement unit (IMU) sensor can be secured to a user's thigh 155, and can generate an absolute angle of the user's thigh 155 or thigh link 102 with respect to vertical gravitational line 161. Since the user's thigh 155 and the thigh link 102 move in unison with each other, leg sensor 128 can be secured to either the user's thigh 155 or thigh link 102. The following describes how exoskeleton 100 is controlled for level ground walking, stairs descent and stairs ascent.

Figure 8:
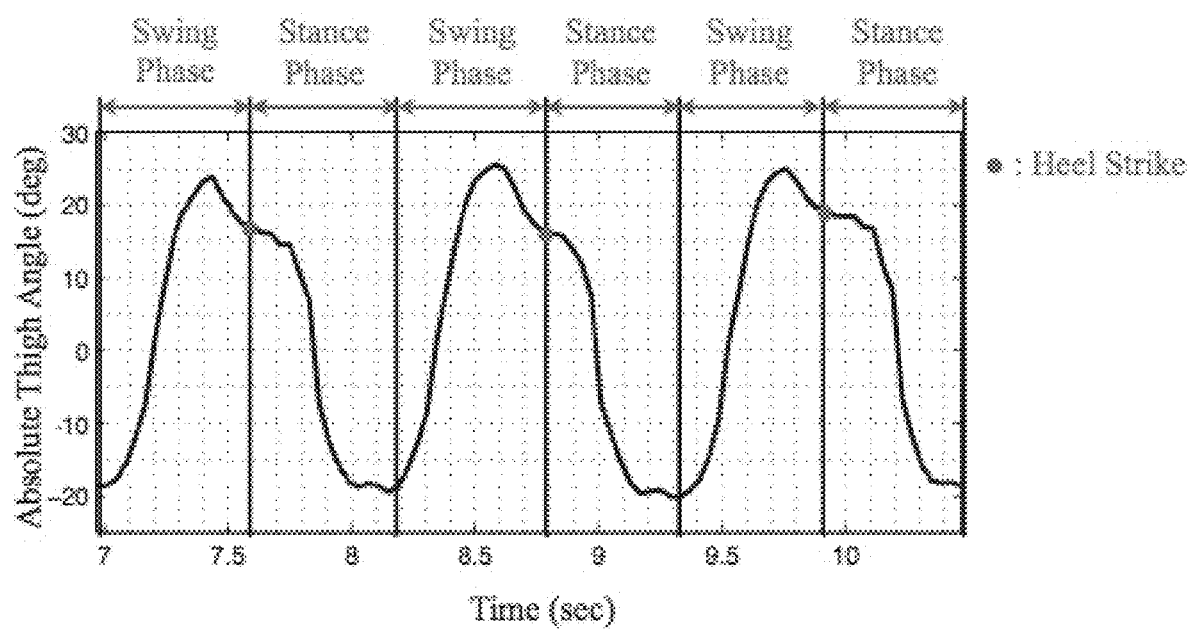
FIG. 8 depicts the absolute thigh angle of a user with respect to a vertical gravitational line.

Level Walking. FIG. 8 shows the absolute angle of a thigh of a person walking on a level ground with respect to vertical gravitational line 161. In one embodiment of the invention, leg signal 140 represents the absolute angle of thigh link 102 relative to vertical gravitational line 161. As can be seen in FIG. 8, in this case, the absolute angle of thigh link 102 relative to vertical gravitational line 161 is confined approximately between −20° and +20 °. These limits may change from person to person and also within a person as a function of time and other variables. Controller 120, based on the value of leg signal 140, controls the resistive torque of torque generator 156.

Figure 9:
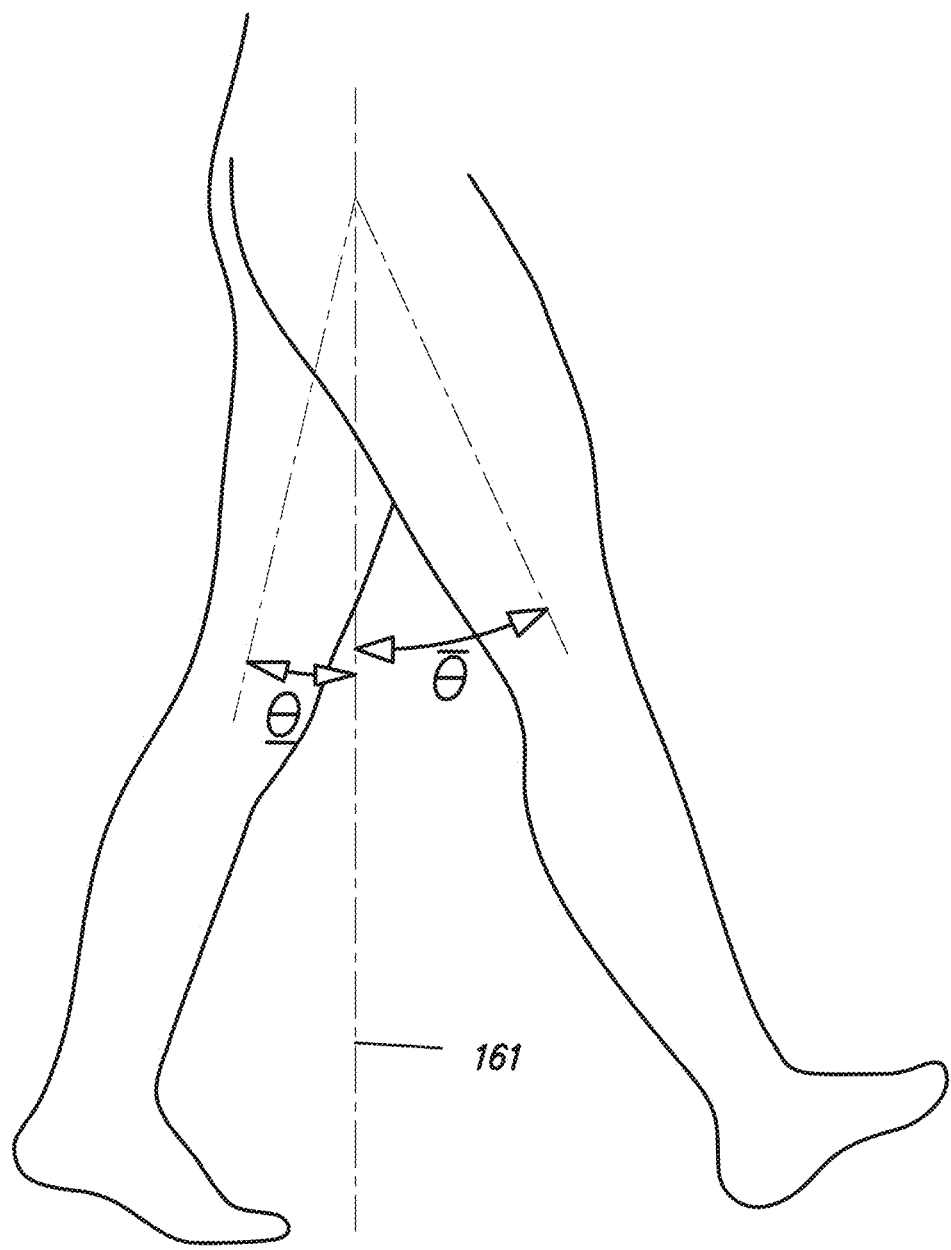
FIG. 9 shows pre-specified maximum and minimum thigh angles.

In operation, torque generator 156 begins to generate a resistive torque in response to flexion when leg signal 140 (in this embodiment, the absolute angle of thigh link 102 with respect to vertical gravitational line 161) becomes larger than a pre-specified maximum thigh angle $\bar{\theta}$. See FIG. 9. This prepares torque generator 156 to generate a resistive torque in response to exoskeleton knee flexion upon heel strike. We define this state of the exoskeleton 100 as "resistive state" 208 (shown in FIG. 12). In some embodiments of the invention, we considered this pre-specified maximum thigh angle $\bar{\theta}$ to be 18°. Depending on the person's gait, this pre-specified maximum thigh angle can be adjusted. Using this method, as soon as leg signal 140 becomes larger than angle $\bar{\theta}$ (e.g. 18°), the exoskeleton will move into resistive state 208 (i.e., provides resistive torque in response to knee flexion) even though the knee joint might still be going through extension.

Figure 12:
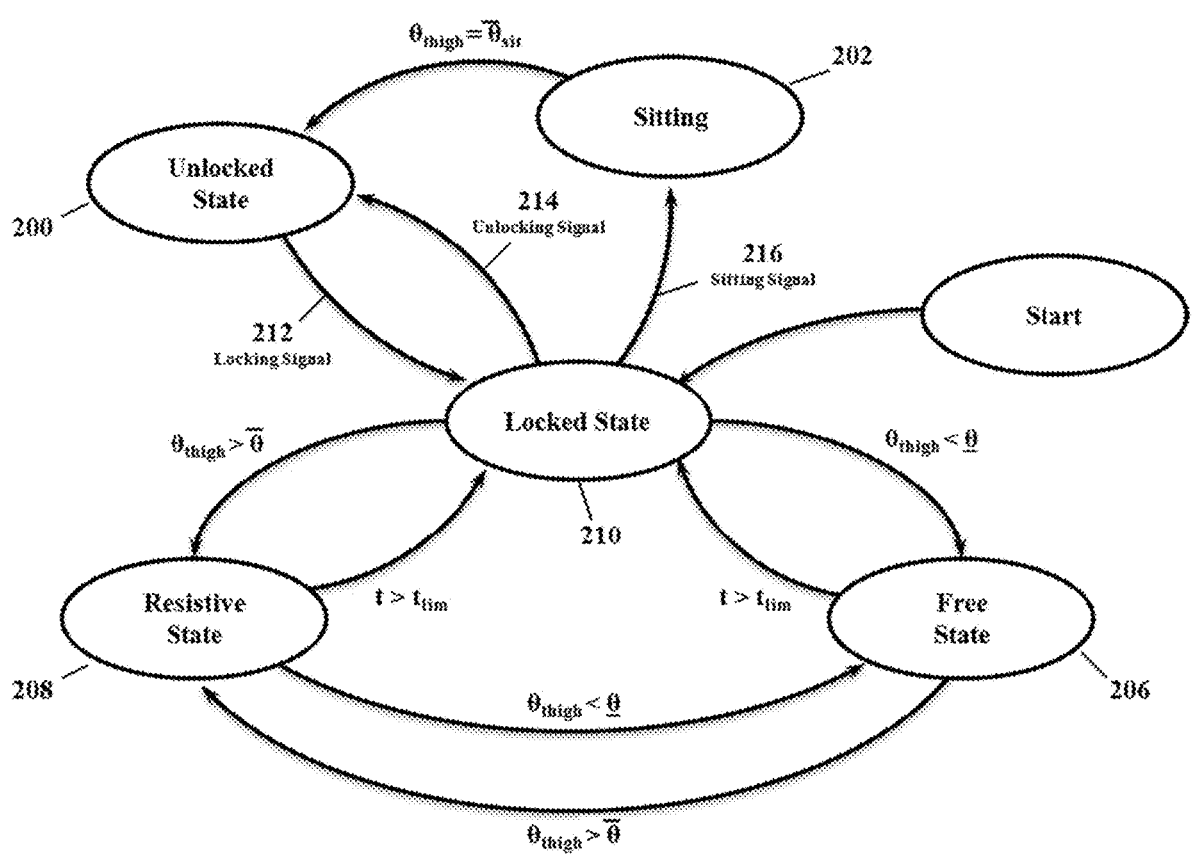
FIG. 12 shows a finite state machine associated with an exoskeleton control.

Torque generator 156 begins to generate zero or a minimum resistive torque when leg signal 140 becomes smaller than a pre-specified minimum thigh angle. This pre-specified minimum thigh angle is represented by $\underline{\theta}$ (shown in FIG. 9). In other words, when leg signal 140 becomes smaller than this minimum thigh angle, torque generator 156 decreases the resistive torque at knee joint 106, which prepares exoskeleton 100 to enter free state. As shown in FIG. 12, we define this state of exoskeleton 100 as "free state" 206. In a preferred embodiment of the invention, torque generator 156 decreases the resistive torque to zero or its minimum possible value. In some embodiments of the invention, we considered this pre-specified minimum thigh angle to be −18°. This pre-specified minimum thigh angle can be adjusted depending on the person's gait.

Figure 10:
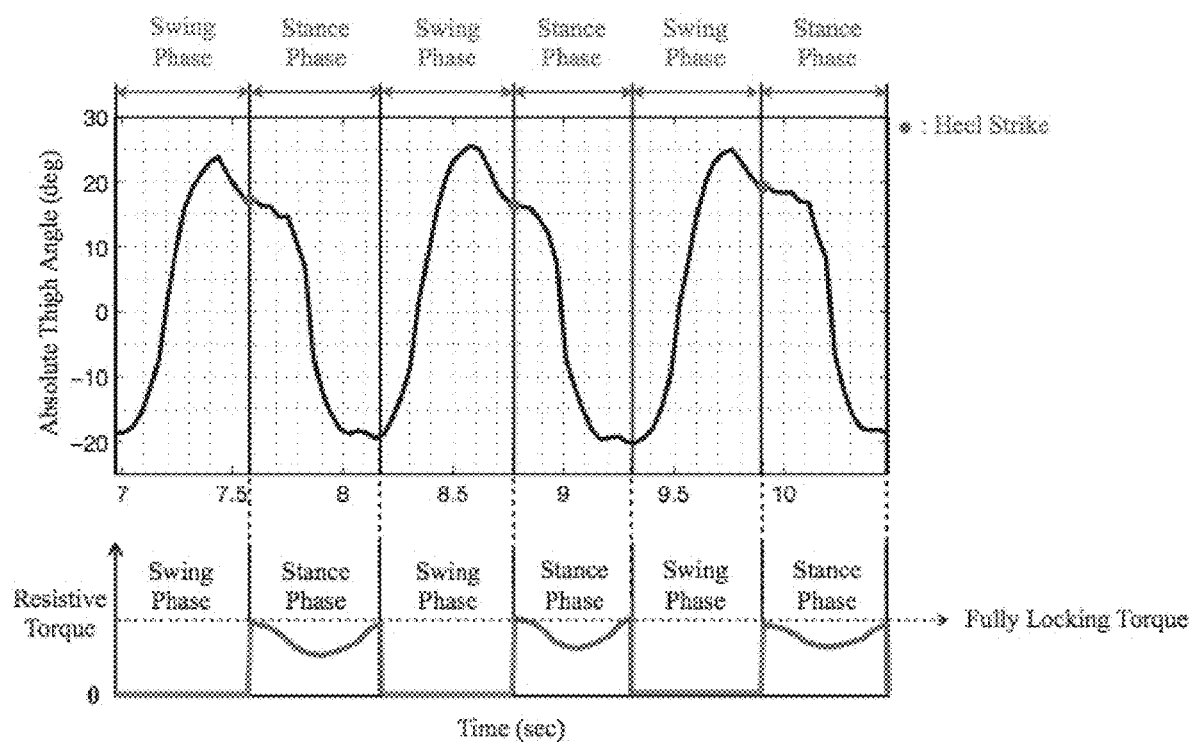
FIG. 10 shows an embodiment of a resistive torque profile.
Figure 11:
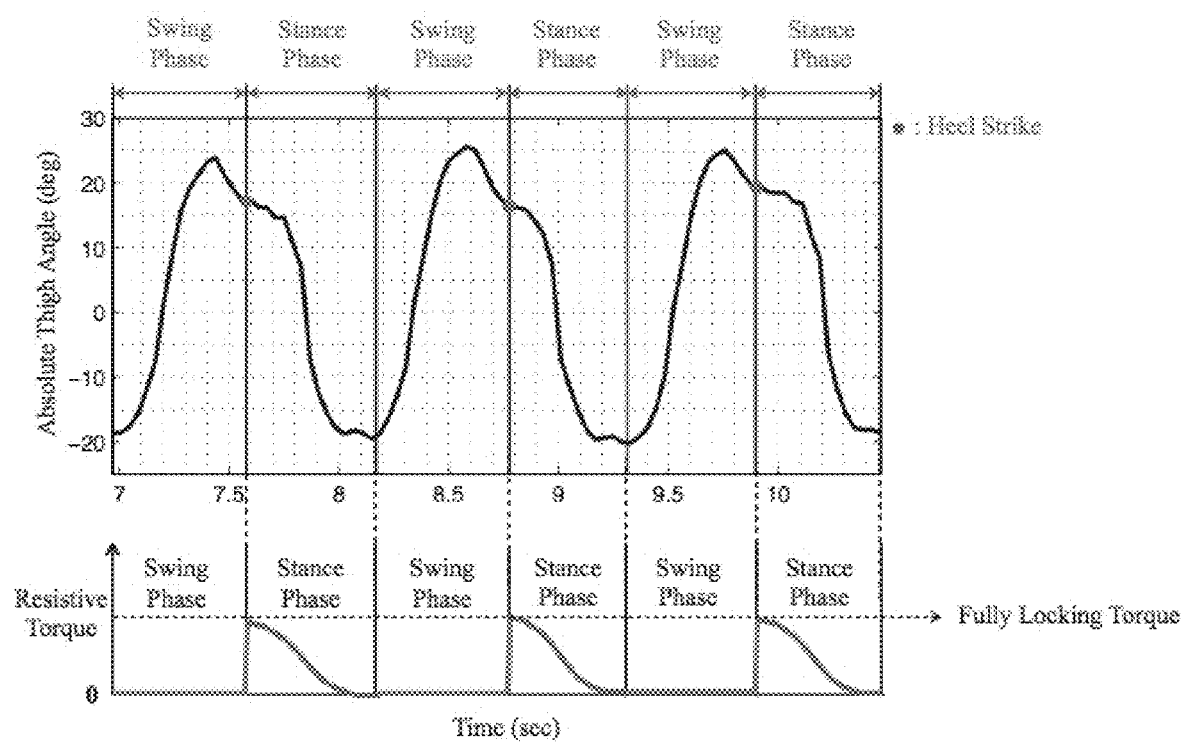
FIG. 11 shows an embodiment of a resistive torque profile.

There are many forms of resistive torque profile during the resistive state 208. As shown in FIG. 10, in some embodiments of the invention, the resistive torque increases to its maximum value very quickly. The resistive torque decreases and then increases again (as a function of leg signal 140 or knee angle or combination of them) just before the toe-off. A profile of this nature may be suitable for persons with mobility disorders. FIG. 11 shows another embodiment of the resistive torque profile which may be used for people with intact mobility. As shown in FIG. 11, resistive torque increases to its maximum value very quickly and then decreases to a minimum value.

FIG. 12 shows the finite state machine associated with the exoskeleton control. As shown in FIG. 12, exoskeleton 100 will move into a locked state 210 where torque generator 156 generates a maximum resistive torque when exoskeleton 100 remains in resistive state 208 for more than a predetermined maximum stance time ($t_{lim}$). In some embodiments of the invention, this predetermined maximum stance time is 1.5 seconds.

Exoskeleton 100 will move into a locked state 210 where torque generator 156 generates a maximum resistive torque when exoskeleton 100 remains in free state 206 for more than a predetermined maximum stance time ($t_{lim}$). In some embodiments of the invention, this predetermined maximum stance time is 1.5 seconds.

In some embodiments of the invention, exoskeleton 100 will move into resistive state 208 when leg signal 140 is larger than a pre-specified maximum thigh angle (i.e., $\theta_{Thigh} > \bar{\theta}$ as shown in FIG. 12). In some embodiments of the invention, exoskeleton 100 will move into free state 206 when leg signal 140 is smaller than a pre-specified minimum thigh angle (i.e., $\theta_{Thigh} < \underline{\theta}$) as shown in FIG. 12).

In some embodiments of the invention, exoskeleton 100 comprises a manual locking device 164 (see FIG. 6), which is capable of generating a locking signal 212 for controller 120. In operation, when manual locking device 164 is activated, exoskeleton 100 will move into a locked state 210 (shown in FIG. 12) where torque generator 156 generates a maximum resistive torque.

In some embodiments of the invention, exoskeleton 100 comprises a manual unlocking device 166 (see FIG. 6) which is capable of generating a manual unlocking signal 214 for controller 120 wherein when manual unlocking device 166 is activated, exoskeleton 100 will move into an unlocked state 200 where torque generator 156 generates a minimum resistive torque. In some embodiments of the invention, the minimum resistive torque has a zero value.

In some embodiments of the invention, exoskeleton 100 comprises a manual sitting device 168 (FIG. 6) capable of generating a manual sitting signal 216 for controller 120. In operation, when manual sitting device 168 is activated, exoskeleton 100 will move into a sitting state 202 where torque generator 156 generates an arbitrary resistive torque appropriate for gradually flexing knee joint 106. In some embodiments of the invention, at the end of sitting state 202, when leg signal 140 reaches a predefined maximum sitting thigh angle value ($\bar{\theta}_{Sit}$) exoskeleton 100 will move into unlocked state 200. In some embodiments of the invention, this predefined maximum sitting thigh angle is about 90 degrees.

Manual locking device 164, manual unlocking device 166, and manual sitting device 168 comprise any signal generator or combination of signal generators capable of generating a manual locking signal 212, manual unlocking signal 214 and manual sitting signal 216 for controller 120. Examples of these signal generators (i.e., 164, 166, and 168) include, without limitation, a switch, momentary switch, toggle switch, on-off button, sliding switch, knob, potentiometer, thumb roll pushbutton and combinations thereof. In some embodiments of the invention, manual locking device 164 and manual unlocking device 166 are the same hardware. One of ordinary skill in the art can understand that there are a variety of methods for generating the above signals through one or more signal generators.

Figure 13:
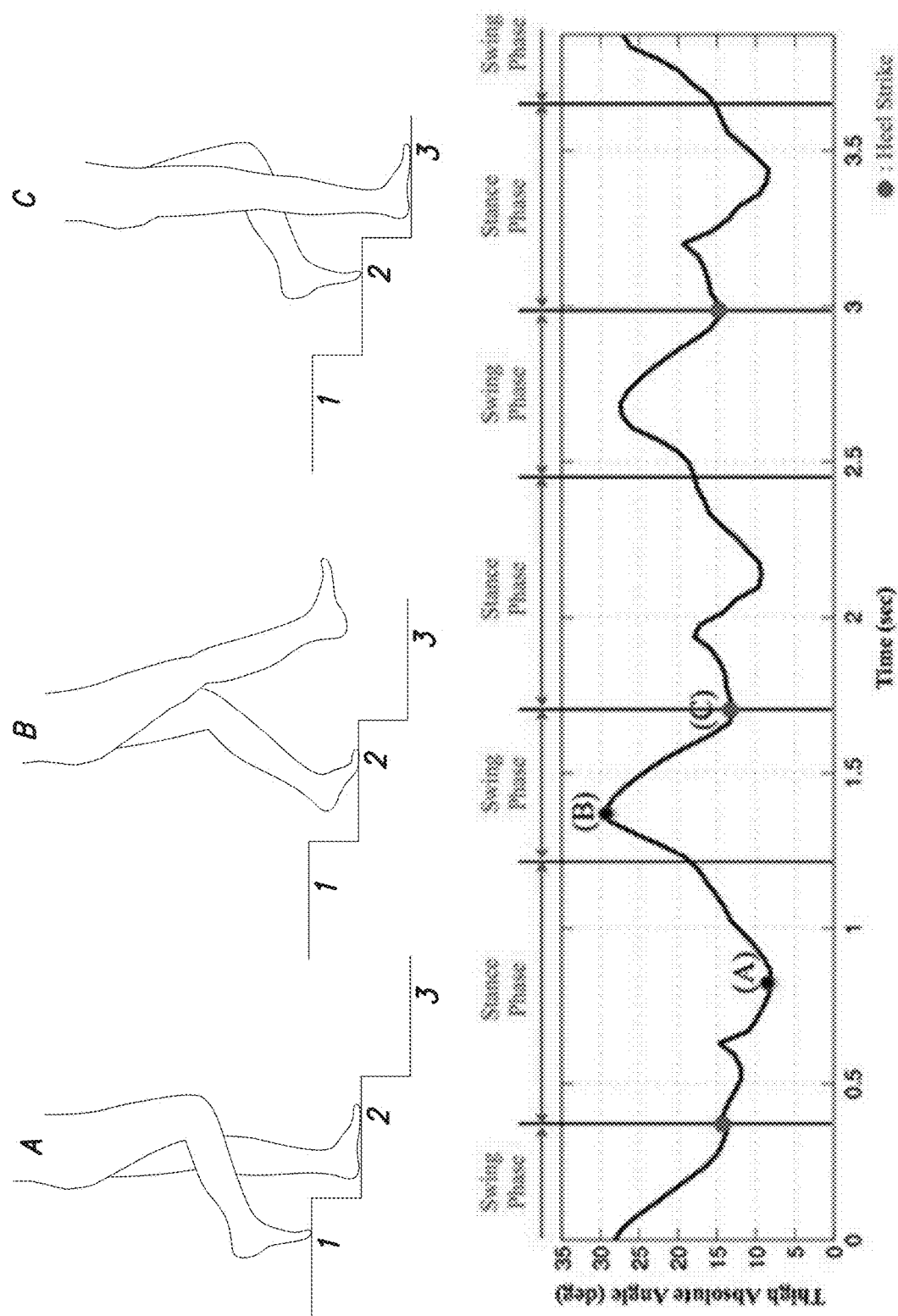
FIG. 13 shows the thigh angle of a user with respect to a vertical gravitational line during stairs descent.
Figure 14:
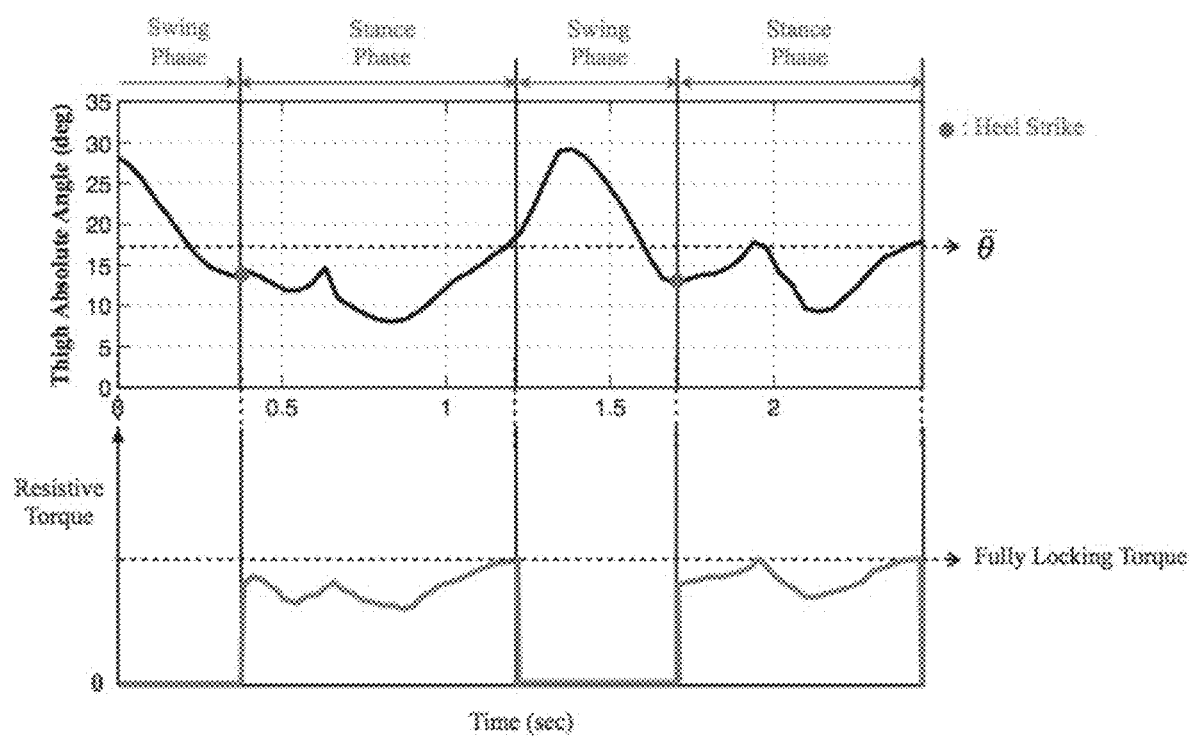
FIG. 14 shows a resistive torque profile during stairs descent.

Stairs Descent. When descending stairs, a person's thigh's absolute angle with respect to vertical gravitational line 161 goes through a periodic motion; however, this thigh absolute angle is always positive. As shown in FIG. 13, during stairs descent, the absolute thigh angle with respect to vertical gravitational line 161 increases to about 30° and decreases to about 12.30°. We have found that if $\underline{\theta}$ and $\bar{\theta}$ are set to operate exoskeleton 100 for level walking (e.g., $\underline{\theta}=-18°$ and $\bar{\theta}=18°$ as described above), exoskeleton 100 can still function when descending stairs. When a thigh angle is detected to be larger than $\bar{\theta}$ (e.g., 18°), exoskeleton 100 moves into resistive state 208 (shown in FIG. 12), although the person's leg is still in swing phase (i.e. not in contact with ground). This means exoskeleton 100 will be ready to create resistive torque in response to knee flexion when the leg contacts the ground. In descending stairs, a person normally does not flex her/his knee during swing phase, since the knee angle has already been flexed substantially during the stance phase. In some embodiments of invention, when descending stairs, exoskeleton 100 does not enter free state 206, since the absolute thigh angle with respect to vertical gravitational line 161 does not decrease to be less than $\underline{\theta}$. This means, in some embodiments of the invention, one set of parameters for $\underline{\theta}$ and $\bar{\theta}$ is sufficient for level ground walking and stairs descent. FIG. 14 shows an embodiment of the resistive torque profile for descending stairs.

With reference back to FIG. 12, when exoskeleton 100 is in the free state 206 and the absolute angle of thigh link 102 with respect to vertical gravitational line 161 is larger than $\overline{\theta}$, exoskeleton 100 will move into resistive state 208. When exoskeleton 100 is in resistive state 208, and the absolute angle of thigh link 102 with respect to vertical gravitational line 161 is less than $\underline{\theta}$, exoskeleton 100 moves into free state 206. A close observation of FIG. 14 and FIG. 12 reveals that during stairs descent, exoskeleton 100 will never enter the free state 206 because the absolute angle of thigh link 102 with respect to vertical gravitational line 161 will never become smaller than $\underline{\theta}$ when descending stairs.

Figure 15B:
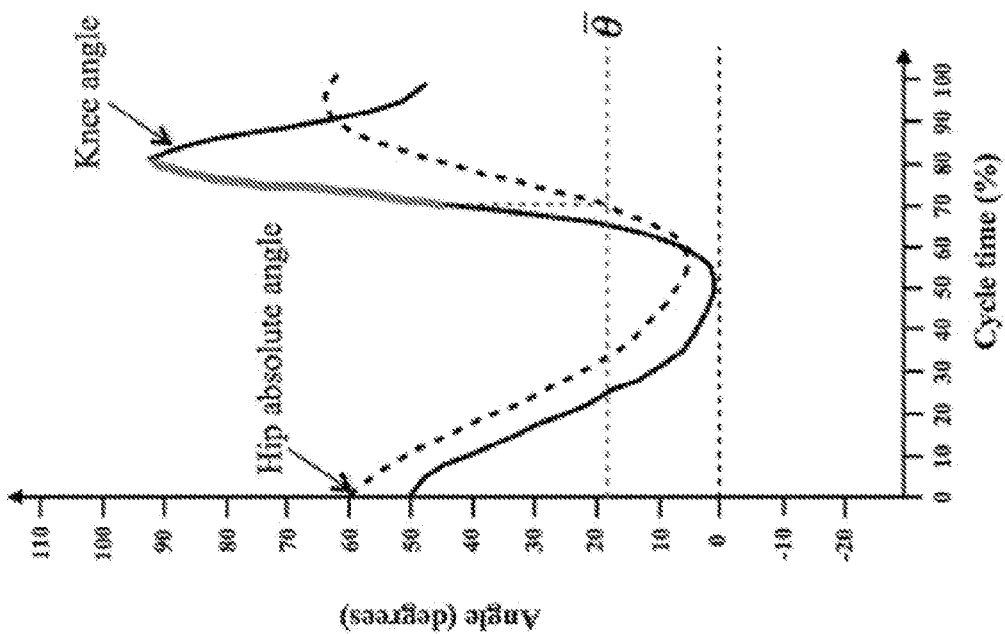
FIGS. 15A and 15B show an absolute thigh angle of a user with respect to a vertical gravitational line during stairs ascent.
Figure 15A:
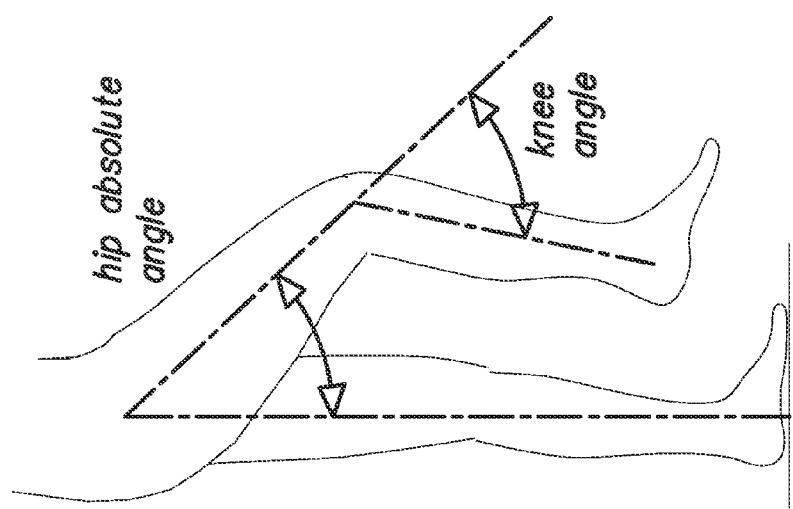

Stairs Ascent. When climbing stairs, a person's thigh angle goes through a periodic motion. FIG. 15 shows a person climbing a set of stairs. It can be observed that once the absolute angle of the person's thigh with respect to vertical gravitational line 161 becomes larger than $\overline{\theta}$ (e.g. 18°), the knee angle (the angle between the thigh and the shank) needs to flex freely to about 90° and then extend to about 50°. Since exoskeleton 100 cannot flex freely when the thigh absolute angle is larger than $\overline{\theta}$, the person's leg may bump into the next step. This means, in some embodiments, we cannot use the same value of $\overline{\theta}$ that we have used during level walking for ascending stairs. Several solutions are offered here. In the first solution, it becomes necessary to use manual unlocking device 166 to move exoskeleton 100 to unlocked state 200 while climbing stairs.

In the second solution, if the knee angle measurement $\theta_{knee}$ is available, then it can be used to differentiate between level walking and stairs ascent. The knee angle measurement, $\theta_{knee}$, represents the angle between the thigh and the shank as shown in FIG. 15. FIG. 15 shows that the knee angle measurement ($\theta_{knee}$) right after toe off, increases from a very small value (almost zero degree) to a large value (somewhere in vicinity of 90°). When the Leg signal 140 reaches $\overline{\theta}$, the knee angle is substantially larger than what it would have been for level walking. The knee angle measurement during level walking is usually about 15° when leg signal 140 reaches $\overline{\theta}$, but the knee angle measurement during stairs ascent is about 45° when leg signal 140 reaches $\overline{\theta}$. When the leg signal 140 reaches $\overline{\theta}$, and the knee angle measurement is smaller than $\overline{\theta}_{knee}$ (i.e., $\theta_{knee}<\overline{\theta}_{knee}$), the controller will move to resistive state 208. In some embodiments of the invention, $\overline{\theta}_{knee}$ is chosen to be 30°, which is a number larger than maximum knee angle measurement during level walking. However, when the leg signal reaches $\overline{\theta}$, and the knee angle measurement is larger than $\overline{\theta}_{knee}$ (i.e., $\theta_{knee}>\overline{\theta}_{knee}$), the controller will remain in its free state 206. The knee angle measurement can be carried out by installation of an encoder or a resolver or any angle sensor in the knee joint.

In the third solution, it becomes necessary to modify $\underline{\theta}$ and $\overline{\theta}$ to appropriate values suited for climbing stairs and slopes. In one embodiment of the invention $\underline{\theta}$ and $\overline{\theta}$ can be set to 10° and 60° for climbing stairs and slopes.

Figure 16:
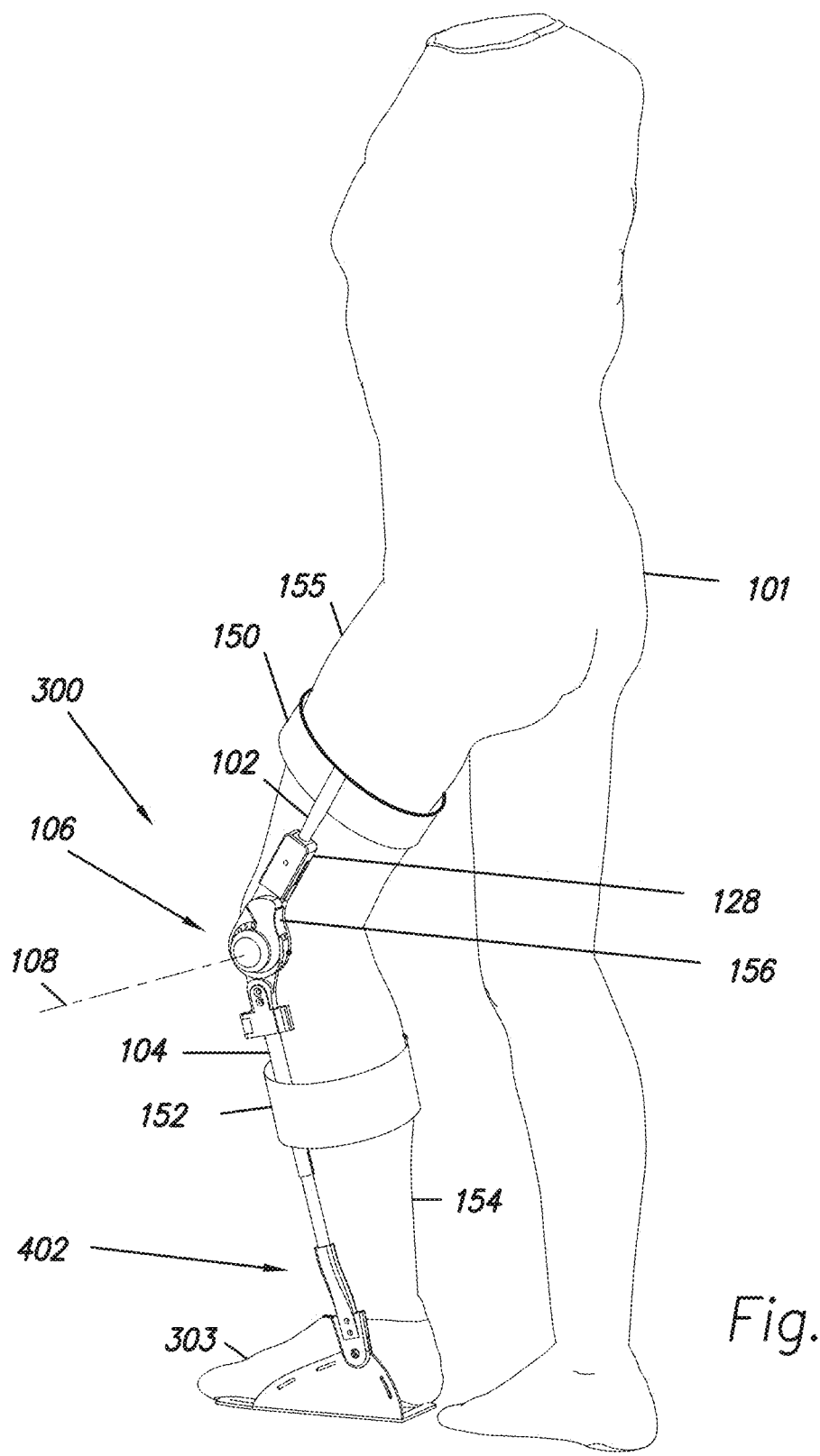
FIG. 16 shows an embodiment of the invention further comprising a first ankle-foot orthosis.
Figure 17:
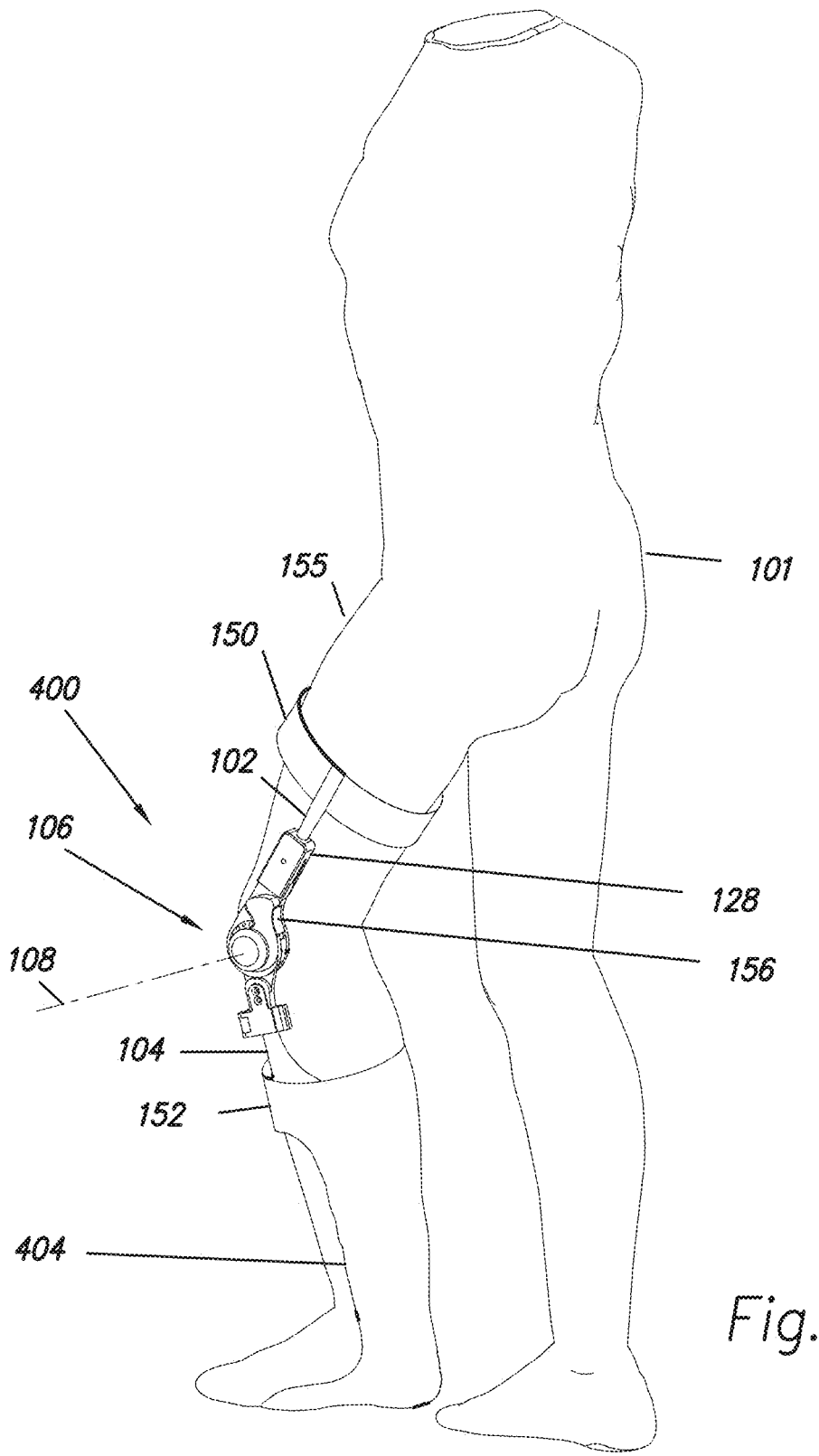
FIG. 17 shows an embodiment of the invention further comprising a second ankle-foot orthosis.
Figure 18:
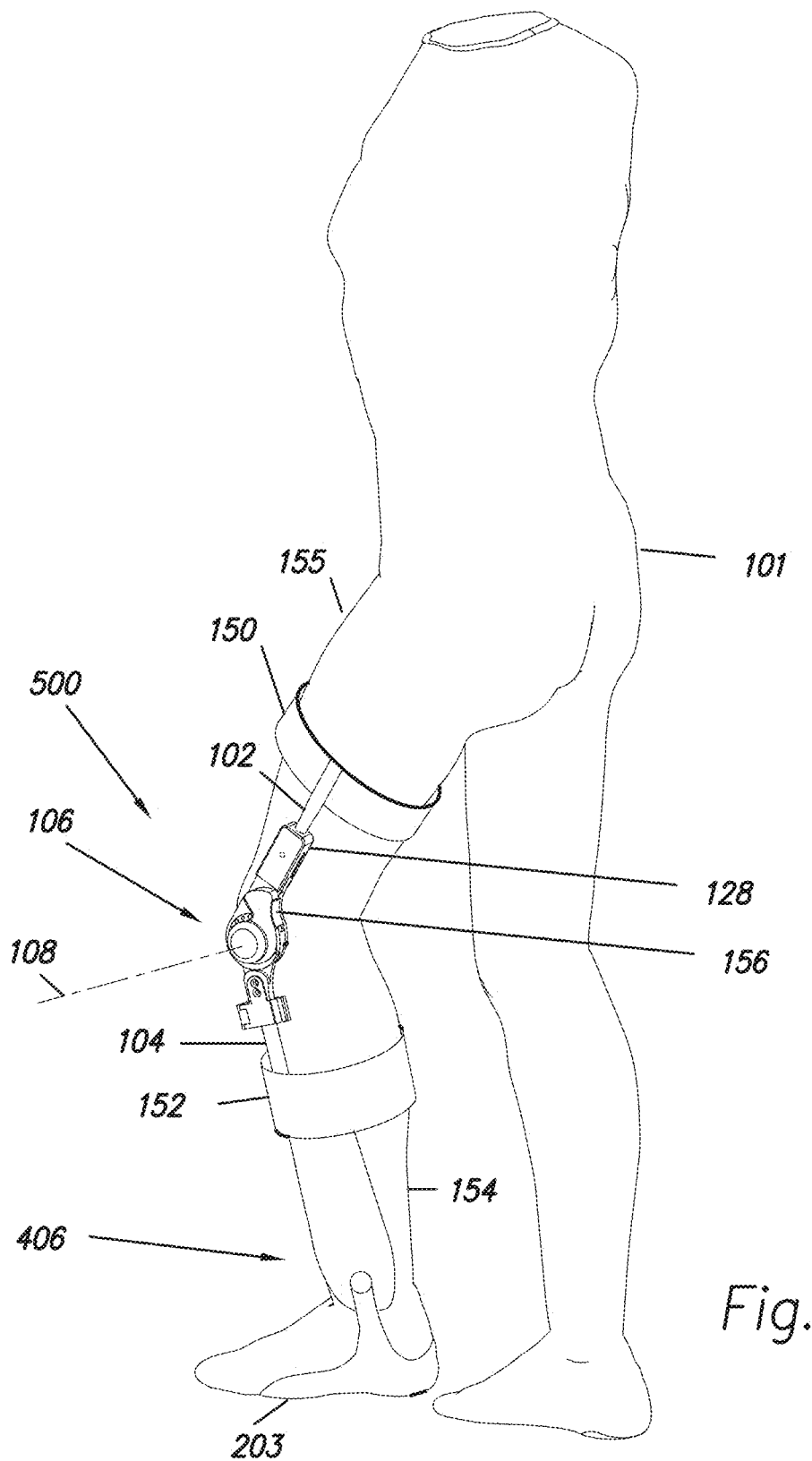
FIG. 18 shows an embodiment of the invention further comprising a third ankle-foot orthosis.
Figure 19:
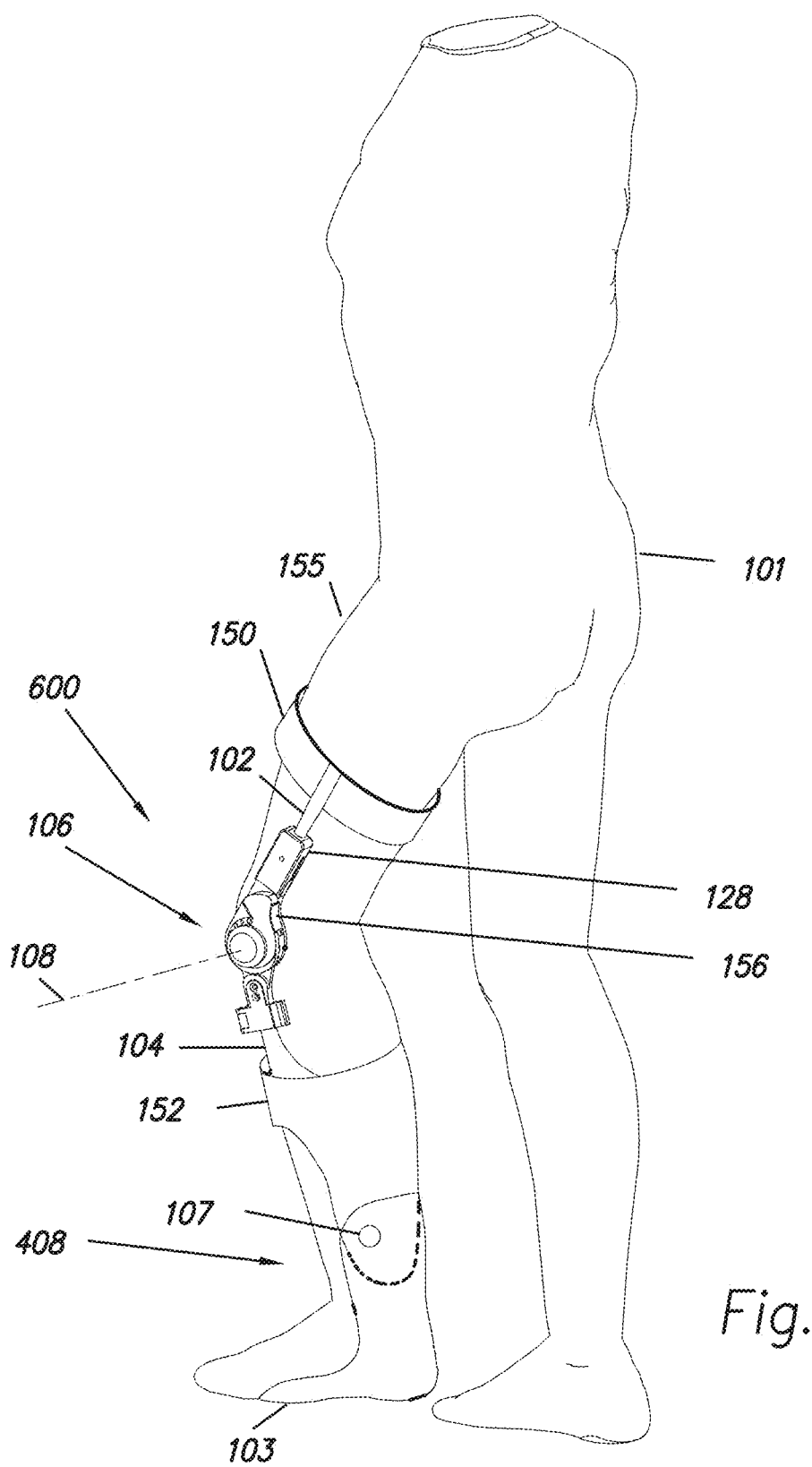
FIG. 19 shows an embodiment of the invention further comprising a fourth ankle-foot orthosis.

FIGS. 16-19 depict embodiments of the invention wherein the exoskeleton further comprises an ankle-foot orthosis. In some embodiments of the invention, such as the embodiment shown in FIG. 16, an ankle-foot orthosis 402 is capable of being coupled to person's foot. In some embodiments of the invention, ankle-foot orthosis 402 is connectable to shank link 104. In some embodiments of the invention, as shown in FIG. 16, exoskeleton 300 further comprises an ankle-foot-orthosis 402, which is worn outside the wearer's shoes 303. In some embodiments of the invention, as shown ion FIG. 17, exoskeleton 400 further comprises an ankle-foot-orthosis 404, which is worn inside the wearer's shoe like an insole (the wearer's shoes are not shown for clarity). An ordinary person skilled in the art can arrive at many forms of internal and external ankle-foot-orthosis. FIG. 18 shows an embodiment of exoskeleton 500 further comprising an ankle-foot-orthosis 406, which is a standard short leg ankle-foot-orthosis (AFO) with fixed (but sometimes adjustable) hinge. This type of AFO is relatively light and easy to fit into shoes. This AFO keeps the foot at any desired angle relative to shank link 104. Further, this AFO does not allow plantar flexion or dorsiflexion, so it doesn't provide quite as natural of a gait as do some other braces. FIG. 17 shows an embodiment of exoskeleton 400 where ankle-foot-orthosis 404 is a standard solid ankle-foot-orthosis. This type of ankle-foot-orthosis stops plantarflexion and also stops or limits dorsiflexion. FIG. 19 shows an embodiment of exoskeleton 600 comprising an ankle-foot-orthosis 408, which is a Plantarflexion Stop AFO. This AFO acts to stop plantarflexion by not letting the foot link 103 point downwards. This type of AFO has a hinge 107 that allows for normal dorsiflexion of foot.

It should be appreciated that, although specific examples of different ankle-foot orthosis are shown, there are other types of ankle-foot-orthosis that could be utilized with the present invention. For example, in some embodiments of the invention, ankle-foot-orthosis is a Dorsiflexion Assist AFO (not shown). This type of AFO is similar to the AFO shown in FIG. 18 but has a spring-like hinge that acts to raise the foot link 203 (dorsiflex the ankle) when the foot comes off of the ground. The Dorsiflexion Assist AFO offers the advantage of a more normal gait pattern. In some embodiments of the invention, the ankle-foot-orthosis is a standard Posterior Leaf Spring ankle-foot-orthosis (not shown). In some embodiments of the invention, the ankle-foot-orthosis is an Energy Return ankle-foot-orthosis (not shown). This type of AFO uses a natural flex built into the material of the AFO to provide assistance in dorsiflexion. These devices are often made of carbon graphite materials. In general, the ankle-foot-orthosis of the present invention comprises any device or combination of internal or external ankle-foot-orthosis capable of performing the indicated functions. Examples of external or internal ankle-foot-orthosis include, without limitation, flexible AFO, rigid AFO, AFO with tamarack flexure, AFO with anti-talus, AFO anti-talus (anterior shell or shell in the front), AFO with a free-motion ankle joint, AFO with an adjustable rigid ankle joint, AFO with a spring-loaded ankle joint, AFO with an adjustable spring-loaded ankle joint and combinations thereof.

Figure 21:
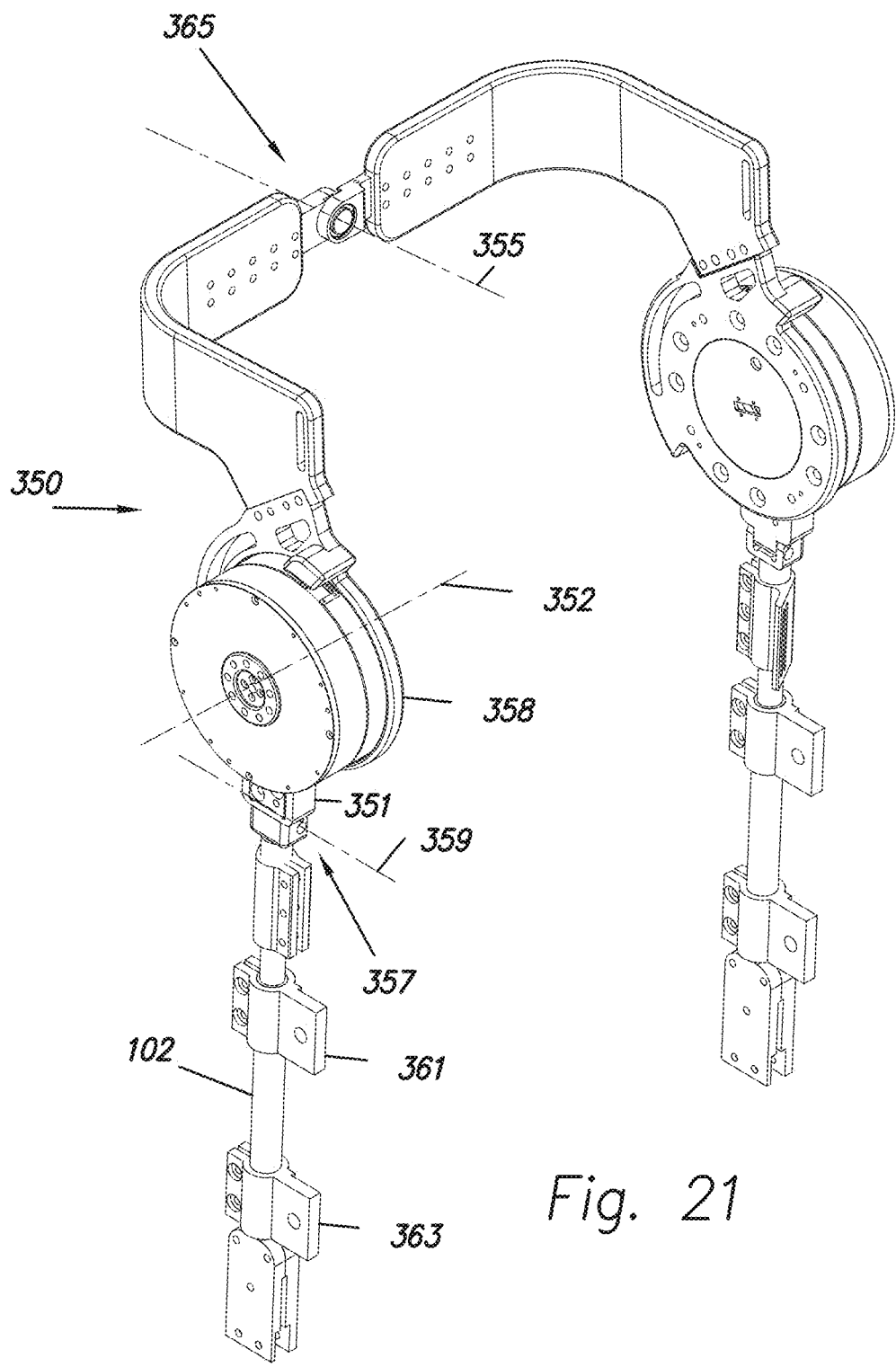
FIG. 21 shows an embodiment of another exoskeleton trunk.

FIGS. 20 and 21 show an embodiment of the invention where exoskeleton 610 further comprises an exoskeleton trunk 350. Exoskeleton trunk 350 is configurable to be coupled to the person's upper body. In some embodiments of the invention, exoskeleton trunk 350 is coupled to a person like a backpack (not shown). In some embodiments of the invention, exoskeleton trunk 350 is coupled to a person like a belt, as depicted in FIG. 20, for example. Exoskeleton trunk 350 comprises a torso link 353 capable of being coupled to person's upper body and torso. Exoskeleton trunk 350 further comprises a trunk thigh link 351 configurable to rotatably couple thigh link 102 to torso link 353. In some embodiments of the invention, trunk thigh link 351 is coupled to thigh link 102. In some embodiments of the invention, trunk thigh link 351 is not coupled to thigh link 102. In an alternative embodiment not shown, trunk thigh link 351 is coupled to person's thigh. In some embodiments of the invention, exoskeleton trunk 350 further comprises an actuator 358 capable of providing torque between torso link 353 and trunk thigh link 351. The controller box 367 and the batteries 369 for the actuators are shown in FIG. 20. In some embodiments of the invention, leg signal 140 represents the absolute angle of thigh link 102 relative to a vertical gravitational line 161 or relative to ground 162. In some embodiments of the invention, leg signal 140 represents the absolute angle of trunk thigh link 351 relative to a vertical gravitational line 161 or relative to ground 162 (see FIG. 6). In some embodiments of the invention, leg signal 140 represents the angle of trunk thigh link 351 with respect to torso link 353 which is substantially parallel with person's torso.

FIG. 21 shows another partial view of the exoskeleton trunk 350. A flexion extension axis 352 represents the flexion and extension between trunk thigh link 351 and torso link 353. In some embodiments of the invention, exoskeleton trunk 350 further comprises a hip abduction-adduction joint 365 allowing for movement between the left side and the right side of exoskeleton trunk 350 relative to each other. An abduction-adduction axis 355 shows the axis of this hip abduction-adduction rotation. In some embodiments of the invention, the abduction-adduction rotation is free to rotate. In some embodiments of the invention, the hip abduction-adduction rotation is impeded by use of a compliant member (not shown). In some embodiments of the invention, the hip abduction-adduction axis can be locked for applications where the abduction and adduction movements in the frontal plane are not encouraged.

In some embodiments of the invention, exoskeleton trunk 350 further comprises a leg abduction-adduction joint 357 allowing for abduction and adduction rotation of trunk thigh link 351 relative to torso link 353'. A leg abduction-adduction axis 359 represents the axis of leg abduction-adduction rotation. In some embodiments of the invention, the leg abduction-adduction rotation is impeded by use of a compliant member such a spring (not shown). In some embodiments of the invention, the leg abduction-adduction motion can be locked in applications where the leg abduction and adduction movements in the frontal plane are not encouraged. FIG. 21 shows tabs 361 and 363, which are used to connect thigh link 120 to brace 150.

Figure 22:
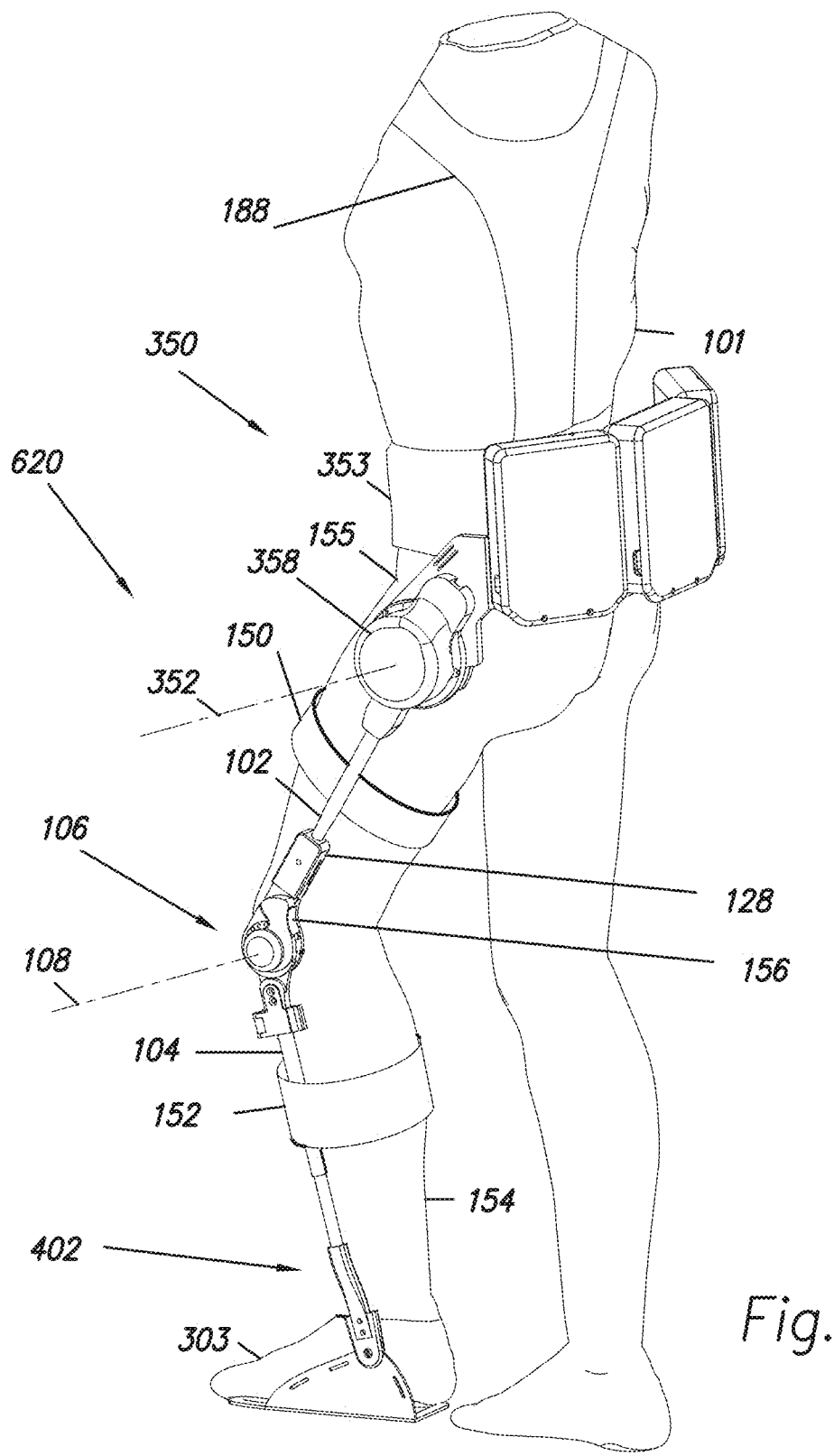
FIG. 22 shows an embodiment of the invention further comprising an exoskeleton trunk including the ankle foot orthosis of FIG. 16.
Figure 23:
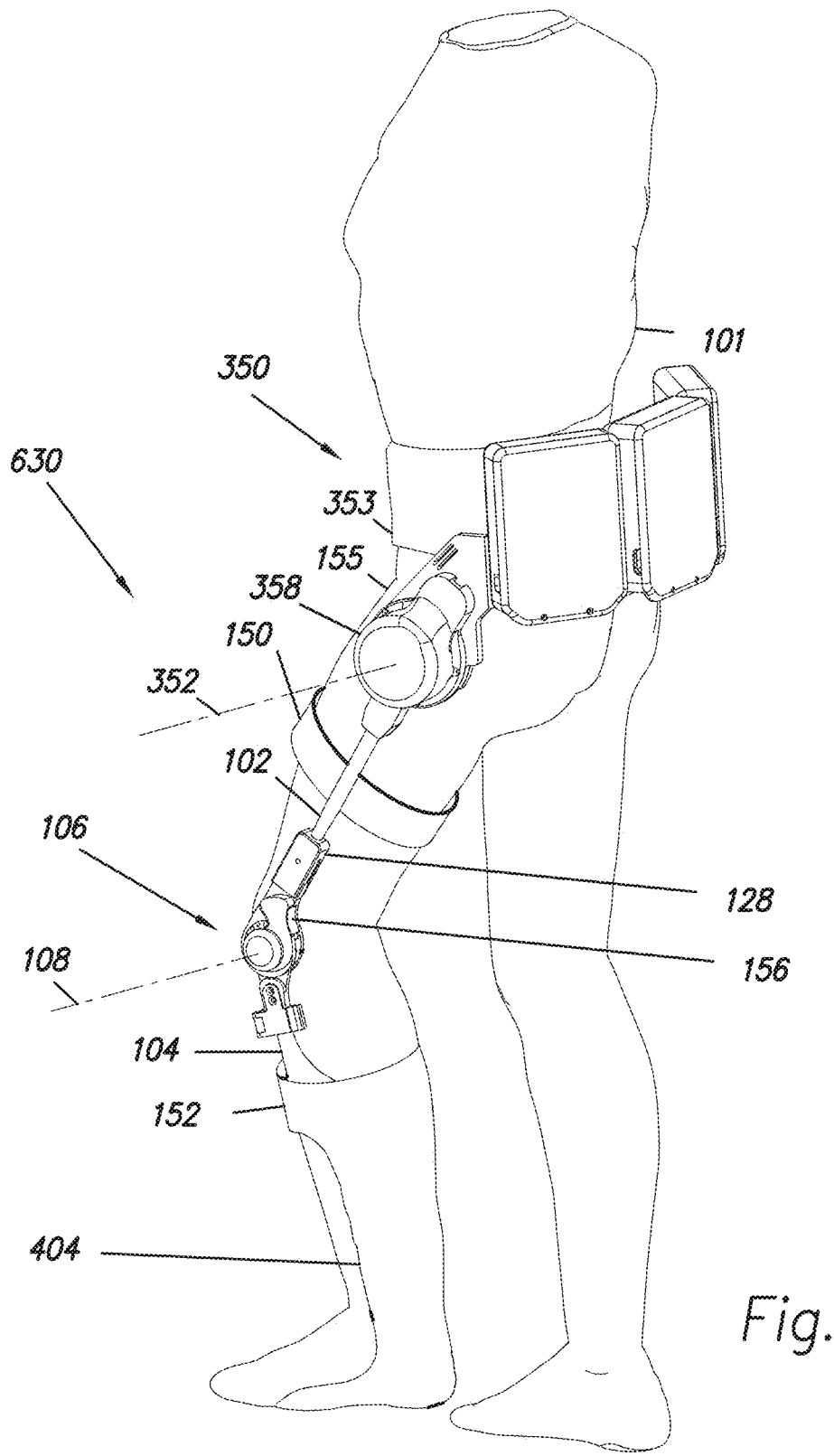
FIG. 23 shows an embodiment of the invention further comprising an exoskeleton trunk including the ankle foot orthosis of FIG. 17.
Figure 24:
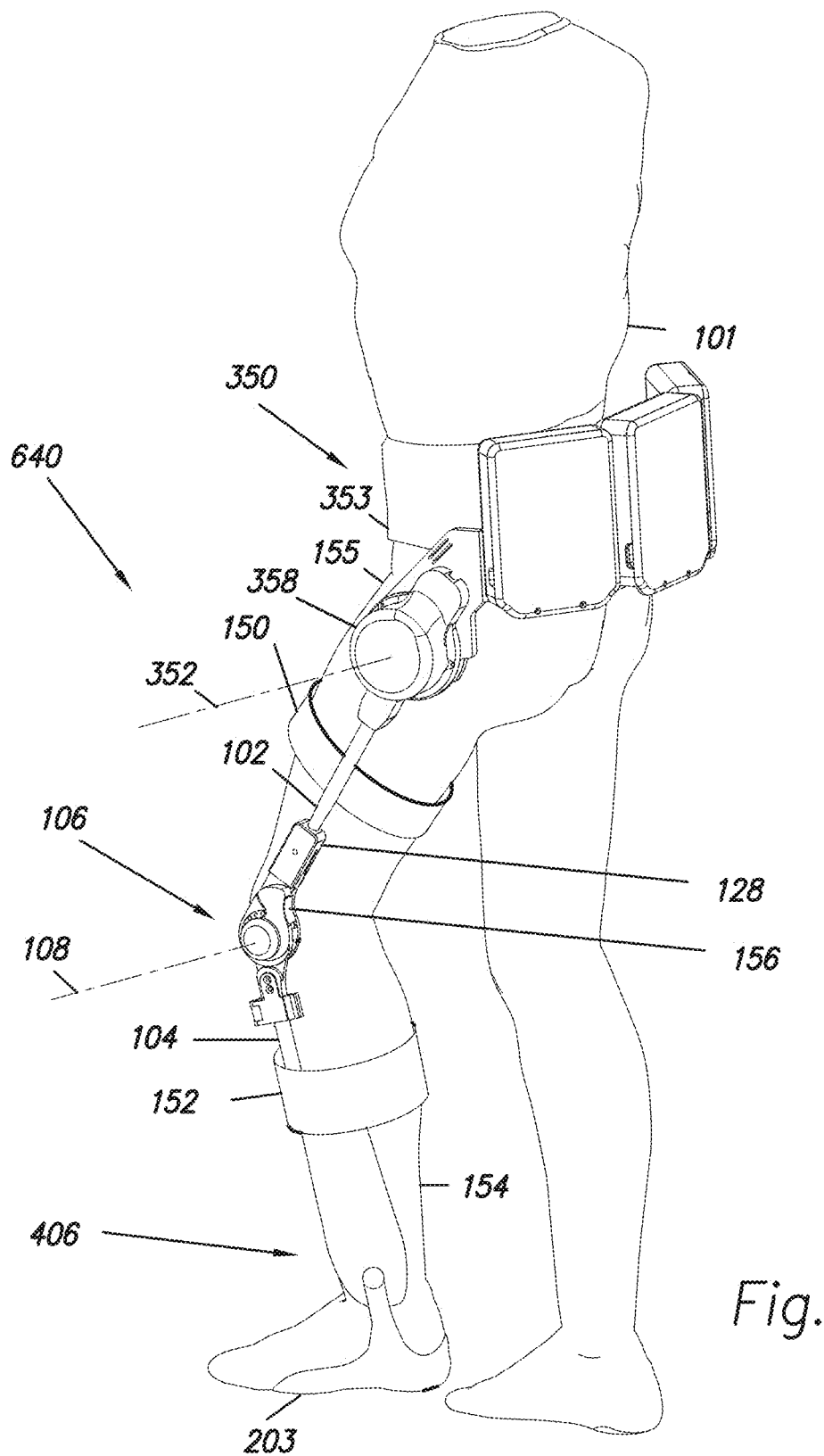
FIG. 24 shows an embodiment of the invention further comprising an exoskeleton trunk including the ankle foot orthosis of FIG. 18.
Figure 25:
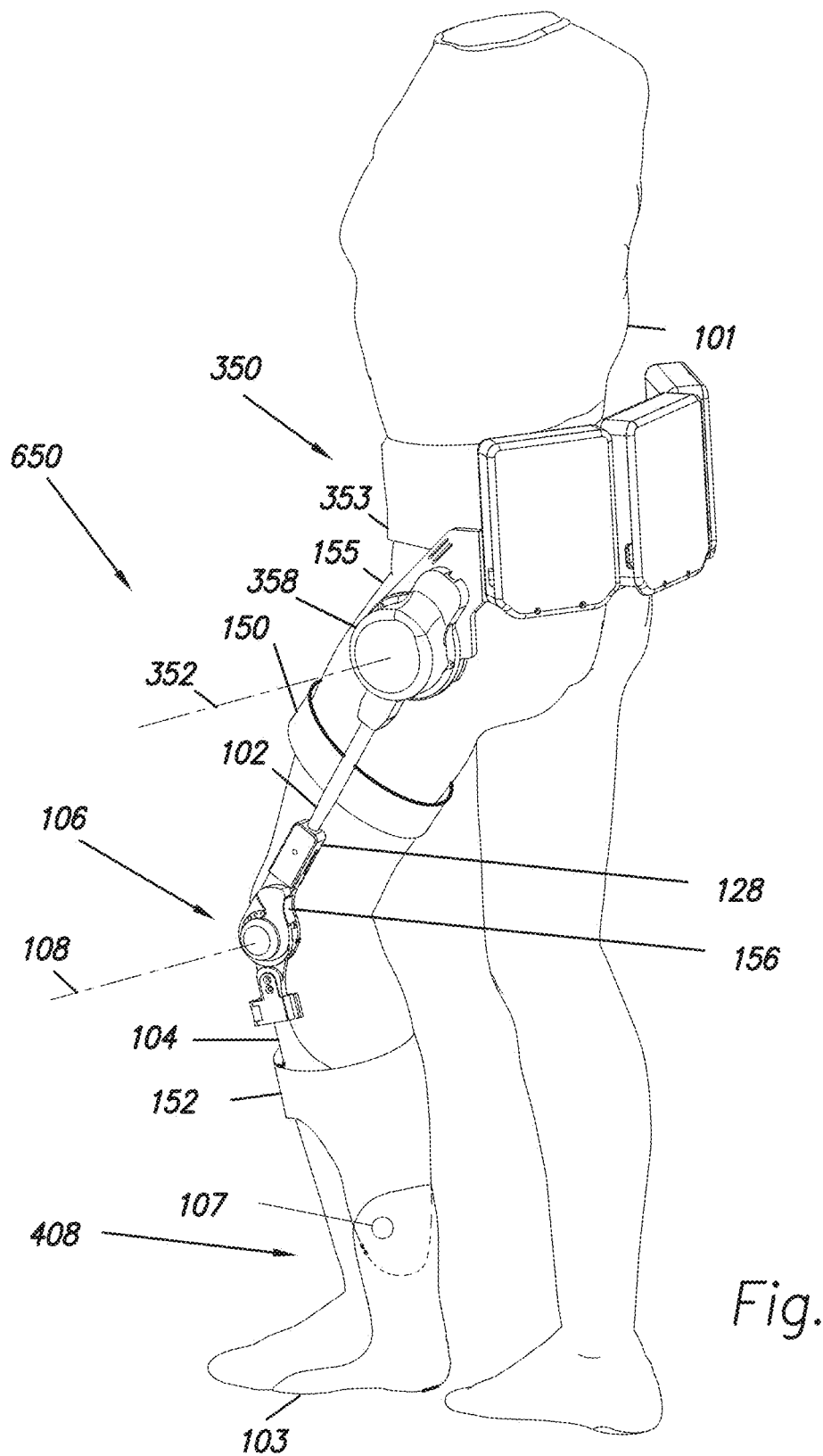
FIG. 25 shows an embodiment of the invention further comprising an exoskeleton trunk including the ankle foot orthosis of FIG. 19.

FIGS. 22-25 depict embodiments of the present invention (exoskeletons 620, 630, 640, and 650) including both an exoskeleton trunk 350 and an ankle-foot orthosis (e.g., 402, 404, 406, and 408). In the embodiments shown, the ankle-foot orthosis of the present invention (404, 406, 408) is capable of being coupled to person's foot and is connectable to shank link 104. Alternatively, in the embodiment depicted in FIG. 22, ankle-foot-orthosis 402 is worn outside the wearer's shoes 303. In some embodiments of the invention, ankle-foot-orthosis 404 is worn inside the wearer's shoe like an insole (as shown in FIG. 23, where the wearer's shoes are not shown for clarity). An ordinary person skilled in the art can arrive at many forms of internal and external ankle-foot-orthosis. FIG. 24 shows an embodiment of exoskeleton 640 where ankle-foot-orthosis 406 is a standard short leg ankle-foot-orthosis with fixed (but sometimes adjustable) hinge. FIG. 23 shows an embodiment of exoskeleton 630 where ankle-foot-orthosis 404 is a standard solid ankle-foot-orthosis. FIG. 25 shows an embodiment of exoskeleton 650 where ankle-foot-orthosis 408 is a Plantarflexion Stop AFO. As previously mentioned, although specific examples of different ankle-foot orthosis are shown, there are other types of ankle-foot-orthosis that could be utilized with the present invention. For example, in some embodiments of the invention, the ankle-foot-orthosis may be a Dorsiflexion Assist AFO. In some embodiments of the invention, the ankle-foot-orthosis may be a standard Posterior Leaf Spring ankle-foot-orthosis. In some embodiments of the invention, the ankle-foot-orthosis may be an Energy Return ankle-foot-orthosis. Exoskeleton trunk 350 is configurable to be coupled to the person's upper body. In some embodiments of the invention, as shown in FIG. 22, exoskeleton trunk 350 is coupled to a person like a backpack using shoulder straps 188. In some embodiments of the invention as shown in FIGS. 23, 24 and 24, exoskeleton trunk 350 is coupled to a person like a belt.

The invention claimed is:

1. An exoskeleton configured to be coupled to a user, said exoskeleton comprising:
    a thigh link, configured to move in unison with a thigh of the user;
    a shank link, configured to move in unison with a shank of the user;
    a knee joint, connected to and positioned between said thigh link and said shank link and configured to allow flexion and extension between said shank link and said thigh link;
    a passive torque generator,
        wherein, when said exoskeleton is in a resistive state, said passive torque generator is configured to create a resistive torque-between said thigh link and said shank link along flexion direction, and
        wherein, when said exoskeleton is in a free state, said passive torque generator is configured to generate a second torque, smaller than said resistive torque;
    at least one leg sensor, configured to create at least one leg signal representing an angle of said thigh link relative to a vertical gravitational line; and
    a controller, in communication with said passive torque generator, wherein said controller is configured to control said passive torque generator based on said at least one leg signal, and
    wherein the controller is configured to move said exoskeleton to said resistive state in response to knee flexion upon heel strike, 1) when said user's leg is in swing phase and not in contact with the ground, 2) when said exoskeleton is in the free state, and 3) when said at least one leg signal is larger than a pre-specified maximum thigh angle.

2. The exoskeleton of claim 1,
    wherein said controller is adapted to move said exoskeleton to the free state where said passive torque generator is configured to generate a zero torque when said exoskeleton is in said resistive state, and
    said at least one leg signal is less than a pre-specified minimum thigh angle.

3. The exoskeleton of claim 2,
    wherein the controller is adapted to move the exoskeleton into a locked state when said exoskeleton remains in said free state for more than a predetermined maximum swing time,
    wherein, in said locked state, said passive torque generator is configured to generate a maximum resistive torque.

4. The exoskeleton of claim 3, wherein said controller is adapted to move said exoskeleton into said free state when said at least one leg signal is smaller than the pre-specified minimum thigh angle.

5. The exoskeleton of claim 1,
    wherein said passive torque generator comprises a first friction surface and a second friction surface,
    wherein said passive torque generator is configured to create the resistive torque between said thigh link and said shank link by use of a friction force between the first friction surface and the second friction surface, wherein said exoskeleton further comprises an electric actuator, wherein said first friction surface is an outer surface of a cylinder coupled to said shank link, wherein said second friction surface is an inner surface of a wrap spring coupled to said thigh link from a first end of said wrap spring, and wherein said electric actuator, by moving a second end of said wrap spring, is configured to control a pressure between said outer surface of said cylinder and said inner surface of said wrap spring.

6. The exoskeleton of claim 5, wherein said electric actuator is coupled to said second end of said wrap spring such that said second end of said wrap spring is unconstrained by said electric actuator and is free to move for unraveling said wrap spring.

7. The exoskeleton of claim 5, wherein said electric actuator is coupled to said thigh link.

8. The exoskeleton of claim 1, wherein when said at least one leg signal reaches a predefined maximum sitting thigh angle value, said exoskeleton will move into an unlocked state, wherein, in said unlocked state, said passive torque generator is configured to generate a zero resistive torque.

9. The exoskeleton of claim 8, wherein said predefined maximum sitting thigh angle is about 90 degrees.

10. The exoskeleton of claim 1, further comprising an ankle-foot orthosis (AFO) capable of being coupled to a foot of the user.

11. The exoskeleton of claim 10, whey said ankle-foot orthosis is connectable to said shank link.

12. The exoskeleton of claim 10, wherein said ankle-foot-orthosis comprises an internal or external ankle-foot-orthosis or a combination of internal or external ankle-foot-orthoses selected from the group consisting of a rigid AFO, a hinged AFO, a non-hinged AFO, a Plantarflexion Stop AFO, a standard posterior leaf spring AFO, an energy return AFO, a flexible AFO, a rigid AFO, an AFO with tamarack flexure, an AFO anti-talus (anterior shell or shell in the front), an AFO with a free-motion ankle joint, an AFO with an adjustable rigid ankle joint, an AFO with a spring-loaded ankle joint, and an AFO with an adjustable spring-loaded ankle joint.

13. The exoskeleton of claim 1,
wherein said thigh link comprises a thigh connector to couple said thigh link to the thigh of the user, and
wherein said shank link comprises a shank connector to couple said shank link to the shank of the user.

14. The exoskeleton of claim 1, wherein said knee joint is free to extend at all times.

15. The exoskeleton of claim 1, wherein said at least one leg sensor comprises an element selected from the group consisting of potentiometers, magnetic encoders, optical encoders, linear variable differential transformers, capacitive displacement sensors, eddy current proximity sensors, variable-inductance proximity sensors, rocker switches, slide switches, accelerometer, inertial measurement units, gyroscopes, magnetometer, and combinations thereof.

16. The exoskeleton of 1, wherein said controller is adapted to move said exoskeleton to the free state when said exoskeleton is in said resistive state and said at least one leg signal is less than a pre-specified minimum thigh angle.

17. The exoskeleton of claim 1, further comprising a knee sensor, measuring an angle between said thigh link and said shank link such that the resistive torque created by the passive torque generator is further based on the angle between said thigh link and said shank link;

wherein said controller is adapted to move said exoskeleton to solid resistive state when said knee sensor indicates flexion between said thigh link and said shank link.

18. The exoskeleton of claim 1 wherein the controller is adapted to move the exoskeleton into a locked state when said exoskeleton remains in said resistive state for more than a predetermined maximum stance time, wherein, in said locked state, said passive torque generator is configured to generate a maximum resistive torque.

19. The exoskeleton of claim 1, further comprising a manual locking device capable of generating a locking signal for said controller, such that when said manual locking device is activated by said user, said exoskeleton is configured to move into a locked state, wherein, in said locked state, said passive torque generator is configured to generate a maxim urn resistive torque.

20. The exoskeleton of claim 1, further comprising a manual unlocking device capable of generating a manual unlocking signal for the controller, such that when said manual unlocking device is activated by said user, said exoskeleton is configured to move into an unlocked state, wherein, in said unlocked state, said passive torque generator is configured to generate a minimum resistive torque.

21. The exoskeleton of claim 1, further comprising a manual unlocking device capable of generating a manual unlocking signal for the controller, such that when said manual unlocking device is activated by said user, said exoskeleton is configured to move into an unlocked state, wherein, in said unlocked state, said passive torque generator is configured to generate a zero resistive torque.

22. The exoskeleton of claim 1, further comprising a manual sitting device capable of generating a manual sitting signal for the controller, such that when said manual sitting device is activated by said user, said exoskeleton is configured to move into a sitting state, wherein, in said manual sitting mode, said passive torque generator is configured to generate an arbitrary resistive torque appropriate for gradually flexing said knee joint.

23. The exoskeleton of claim 1, further comprising a manual locking device capable of generating a locking signal for the controller such that when said manual locking device is activated, said exoskeleton is configured to move into a locked state wherein said passive torque generator is configured to generate a maximum resistive torque.

24. An exoskeleton configured to be coupled to a user, said exoskeleton comprising:

a torso link, capable of being coupled to a torso of the user;

a thigh link, configured to move in unison with a thigh of the user and rotatably coupled to said torso link at a hip of the user;

an actuator, capable of providing torque between said torso link and said thigh link;

a shank link, configured to move in unison with a shank of the user;

a knee joint, positioned between said thigh link and said shank link and configured to allow flexion and extension between said shank link and said thigh link;

a passive torque generator, wherein, when said exoskeleton is in a resistive state, said passive torque generator is configured to create a resistive torque between said thigh link and said shank link along a flexion direction, and wherein, when said exoskeleton is in a free state, said passive torque generator is configured to generate a second torque, smaller than said resistive torque;

at least one leg sensor for creating at least one leg signal, wherein said at least one leg signal is selected from the group consisting of a signal representing an angle of said thigh link relative to a vertical gravitational line, a signal representing an angle of said thigh link relative to the torso link, and combinations thereof; and a controller, in communication with said passive torque generator and is configured to move said exoskeleton to the resistive state in response to knee flexion upon heel strike, 1) when said user's leg is in swing phase and not in contact with the ground, 2) when said exoskeleton is in the free state, and 3) when said at least one leg signal is larger than a pre-specified maximum thigh angle.

25. The exoskeleton of claim 24, wherein said passive torque generator comprises a first friction surface and a second friction surface, wherein the passive torque generator is configured to create the resistive torque between said thigh link and said shank link by use of friction force between the first friction surface and the second friction surface, and wherein said exoskeleton further comprises an electric actuator, wherein said first friction surface is an outer surface of a cylinder coupled to said shank link, wherein said second friction surface is an inner surface of a wrap spring coupled to said thigh link from a first end of said wrap spring, and wherein said electric actuator, by moving a second end of said wrap spring, is configured to control a pressure between said outer surface of said cylinder and said inner surface of said wrap spring.

26. The exoskeleton of claim 24, further comprising an ankle-foot orthosis (AFO) capable of being coupled to a foot of the user.

27. The exoskeleton of claim 24, wherein said controller is adapted to move said exoskeleton to the free state when said exoskeleton is in said resistive state and said at least one leg signal is less than a pre-specified minimum thigh angle.

28. The exoskeleton of 24, wherein said controller is adapted to move said exoskeleton to the free state when said exoskeleton is in said resistive state and said at least one leg signal is less than a pre-specified minimum thigh angle, wherein, in said free state, said passive torque generator is configured to generate a zero torque.

* * * * *